US012241091B2

(12) United States Patent
Ma et al.

(10) Patent No.: US 12,241,091 B2
(45) Date of Patent: Mar. 4, 2025

(54) METHOD OF MAKING EXOSOMES FROM TUMOR CELL/ANTIGEN PRESENTING CELL HYBRID CELLS

(71) Applicant: INSTITUTE OF PROCESS ENGINEERING, CHINESE ACADEMY OF SCIENCES, Beijing (CN)

(72) Inventors: Guanghui Ma, Beijing (CN); Wei Wei, Beijing (CN); Shuang Wang, Beijing (CN); Shuang Qing, Beijing (CN); Jianghua Wang, Beijing (CN)

(73) Assignee: INSTITUTE OF PROCESS ENGINEERING, CHINESE ACADEMY OF SCIENCES, Beijing (CN)

( * ) Notice: Subject to any disclaimer, the term of this patent is extended or adjusted under 35 U.S.C. 154(b) by 1033 days.

(21) Appl. No.: 17/269,897

(22) PCT Filed: Aug. 16, 2019

(86) PCT No.: PCT/CN2019/101079

§ 371 (c)(1),
(2) Date: Feb. 19, 2021

(87) PCT Pub. No.: WO2020/038299

PCT Pub. Date: Feb. 27, 2020

(65) Prior Publication Data

US 2021/0324342 A1 Oct. 21, 2021

(30) Foreign Application Priority Data

Aug. 20, 2018 (CN) ........................ 201810946746.X

(51) Int. Cl.

| | |
|---|---|
| ***C12N 5/00*** | (2006.01) |
| ***A61K 35/15*** | (2015.01) |
| ***A61K 35/17*** | (2015.01) |
| ***A61K 39/00*** | (2006.01) |
| ***A61P 35/00*** | (2006.01) |
| ***C07K 16/28*** | (2006.01) |
| ***C12N 5/0786*** | (2010.01) |
| ***C12N 5/16*** | (2006.01) |

(52) U.S. Cl.

CPC .............. *C12N 5/163* (2013.01); *A61K 35/15* (2013.01); *A61K 35/17* (2013.01); *A61K 39/0011* (2013.01); *A61P 35/00* (2018.01); *C07K 16/2818* (2013.01); *C07K 16/2827* (2013.01); *C12N 5/0645* (2013.01); *A61K 2039/5154* (2013.01); *A61K 2039/572* (2013.01)

(58) Field of Classification Search

None

See application file for complete search history.

(56) References Cited

FOREIGN PATENT DOCUMENTS

| | | |
|---|---|---|
| CN | 1446583 | * 10/2003 |
| JP | H11290068 | * 10/1999 |

OTHER PUBLICATIONS

CN 1446583 translation, 2003.*
JPH11290068 translation, 1999.*

* cited by examiner

*Primary Examiner* — Michael C Wilson
(74) *Attorney, Agent, or Firm* — HAUPTMAN HAM, LLP

(57) ABSTRACT

Provided is an exosome, which is secreted by a hybrid cell formed by antigen-presenting cells phagocytosing the cell nuclei of tumor cells. Using the strategy of macrophages phagocytosing the cell nuclei of tumor cells achieves endogenous expression of tumor antigens on macrophages, and the exosome prepared has good capabilities of targeting to lymph nodes and tumors dually.

3 Claims, 11 Drawing Sheets

METHOD OF MAKING EXOSOMES FROM TUMOR CELL/ANTIGEN PRESENTING CELL HYBRID CELLS

RELATED APPLICATIONS

The present application is a National Phase of International Application Number PCT/CN2019/101079 filed Aug. 16, 2019 and claims priority to Chinese Application Number 201810946746.X filed Aug. 20, 2018.

TECHNICAL FIELD

The disclosure relates to an exosome, a preparation method thereof, and a method of antitumor immunotherapy based on the exosome, wherein the exosome has dual effects of immune activation and tumor microenviromnent regulation.

BACKGROUND ART

There are usually three therapeutic means for malignant tumors: surgical treatment, radiotherapy and chemotherapy, respectively. Among them, the surgical treatment is limited to direct excision of solid tumors that are visible to the naked eyes to achieve the therapeutic effect, and furthermore, the surgical treatment can not ensure that all of the tumor cells are removed due to the extremely strong infiltration of malignant tumors and thus there is a relatively high risk of tumor recurrence. The radiotherapy utilizes radioactive rays (such as α-rays, β-rays, γ-rays, etc.) with the cell-killing ability to irradiate the sites of malignant tumors to kill cancer cells. The ray radiotherapy will inevitably produce certain adverse effects on surrounding tissues and cells during the irradiation due to its lack of specificity. The chemotherapy utilizes a chemical drug with the tumor killing ability to kill tumor cells, thereby effectively inhibiting the proliferation, spread and metastasis of tumor cells. However, the vast majority of the chemotherapeutic drugs do not have the ability to specifically kill tumors, they can also cause damage to normal cells of the body while killing tumors and have strong side effects.

With the development of tumor biology and immunology, the immunotherapy mainly characterized by regulating the body's own immune system has opened up a new idea for tumor treatment. The tumor immunotherapy stimulates and enhances the body's own immune protection mechanisms to kill abnormal tumor cells using various means, thereby achieving the purpose of treating tumors and preventing recurrence. Currently, certain research progresses have been made in adoptive therapies of lymphocytes, antibody therapies, therapeutic antitumor vaccines, and antitumor immunotherapies represented by immune checkpoint blocking therapies.

The basic principle of a therapeutic antitumor vaccine for treating tumors is the activation of the patient's own immune system through the vaccine comprising tumor antigen, which can subsequently produce a specific immune response against tumor cells and finally achieve specifical tumor cells elimination. The process starts with the uptake of tumor antigens by antigen-presenting cells (APC), and is completed by the cooperation of various immune cells with the aid of a complex immune factor signaling network. Firstly, the tumor antigens at the tumor site will be recognized by the patrolling APCs, these APCs will uptake tumor antigen and accomplish antigen presentation on their MHC molecules. Meanwhile the APCs will release a large number of chemokines to attract more APCs to the injection site for the uptake, processing and presentation of the tumor antigens. The APCs activated by a tumor vaccine actively home to lymph nodes, and activate the $CD4^+$ T and the $CD8^+$ T lymphocytes respectively in the lymph nodes: on the one hand, the APCs can activate the $CD8^+$ T lymphocytes through the MHC I complex on the surface of the APCs to promote the $CD8^+$ T lymphocytes proliferation and further transformation into cytotoxic T lymphocytes (CTLs) with the tumor cell killing effect, then the CTLs migrate and infiltrate the tumor site, lyse and kill the tumor cells, thus achieving the purpose of complete elimination of the tumor cells through above cellular immune response; on the other hand, the APCs can activate the $CD4^+$ T lymphocytes through the MHC II complex on the surface of the APCs to induce humoral immune response, and the $CD4^+$ T lymphocytes are transformed into Th1 type helper T cells which help the CTLs exert the tumor cell killing effect by secreting Th1 type cytokines (such as IFN-γ).

Currently, many new nano-tumor vaccines have been proved in in-vitro experiments that they can achieve above-mentioned cellular immune response and production of a large number of CTLs; however, their tumor inhibition effects at the animal level are not ideal, which is mainly due to the complex tumor microenvironment existing in the tumor sites in animals. A large number of immunosuppressive cells exist in the tumor microenvironment, including: tumor-associated macrophages (TAMs), myeloid-derived suppressor cells (MDSCs), regulatory dendritic cells (DC-regs) and regulatory T cells (Tregs), etc. These immunosuppressive cells, usually by means of the immunosuppressive molecules (such as PD-L1) on their surface or by secreting a large number of inhibitory cytokines (such as IL-10 and TGF-β), prevent the sensitization and reduce the infiltration ability of effector lymphocytes, and inhibit the infiltrating effector cells from exerting their killing effect, thereby weakening the body's antitumor immunity.

Despite the various studies as mentioned above, it would be of great significance for clinical application to develop such a vaccine that can more efficiently stimulate the body to produce specific immunity, for example, the vaccine having the capabilities of targeting the tumor sites and improving the tumor immunosuppressive microenvironment in addition to the capability of activating the cellular immune response in the body.

SUMMARY OF THE DISCLOSURE

The inventors of the present application found that the endogenous expression of tumor antigens on APC can fundamentally achieve the MHC I presentation of tumor antigens, and meanwhile can achieve the efficient expression of costimulatory factors (such as CD40, CD80, CD86, etc.) on APC. For example, macrophages having a strong phagocytic ability are used to phagocytose the nuclei of tumor cells, the formed "hybrid" cells are stimulated with lipopolysaccharide (LPS), and then exosomes are extracted from the resulting hybrid macrophages, thus obtaining an exosome-based vaccine formulation with the similar functions of APC. Since the nuclei of tumor cells contains complete genetic information of the tumor cells, the nuclei of tumor cells after being endocytosed will utilize the organelles of macrophages to endogenously express the MHC I complex of tumor antigens on the macrophage membrane; the co-stimulation of LPS during the culture process can further increase the expression level of costimulatory molecules and tumor antigen-MHC I complex on the surface of the macrophages, and at the same time can facilitate the transformation of the macrophages into M1-type macrophages with the antitumor effect. A large number of costimulatory molecules, tumor antigen-MHC I complexes and a variety of antitumor related signaling molecules for immune activation are carried on the hybrid exosomes secreted by such activated "hybrid" cells. These hybrid exosomes are similar to nano-scale APC; because of their nano-scale particle sizes, some exosomes can target lymph nodes and simulate the APC function in the lymph nodes, and directly activate T cells and elicit cellular immune response. In addition, since the hybrid exosomes carry certain tumor signals (such as adhesion molecules) which contribute to the homologous tumor targeting, some exosomes can be guided to the tumor sites through the directed chemotaxis of the homologous tumors. The hybrid exosomes within the tumors may rely on their internal immune activating signaling molecules to reversely transform the M2-type macrophages to M1-type macrophages, reduce the proportion of Tregs, and thus improve the tumor microenvironment.

On this basis, the disclosure provides a hybrid cell formed by a kind of antigen-presenting cell phagocytosing the nucleus of a kind of tumor cell. Preferably, the antigen-presenting cell is dendritic cell, macrophage or B cell.

The disclosure also provides an exosome which is a nano-cell vesicle secreted by the hybrid cell, and the exosome is a hybrid exosome.

The disclosure also provides a method for preparing an exosome, comprising the steps of: extracting the nucleus from tumor cell, adding the nucleus of the tumor cell into a culture fluid of the antigen-presenting cell, incubating, then collecting a supernatant of the culture fluid, and performing differential centrifugation to collect the exosome.

The disclosure also provides a pharmaceutical composition, comprising the hybrid cell or exosome as mentioned and a pharmaceutically acceptable carrier, and the pharmaceutical composition is, for example, an antitumor vaccine.

The disclosure also provides a pharmaceutical composition, comprising the exosome as mentioned, a monoclonal antibody, and a pharmaceutically acceptable carrier, wherein the monoclonal antibody is, for example, a PD-1 antibody, a PD-L1 antibody or a CTLA-4 antibody.

DETAILED DESCRIPTION OF EMBODIMENTS

Figure 1:
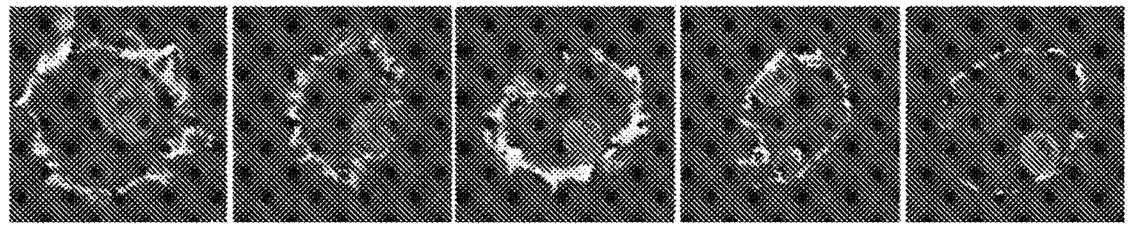
FIG. 1 shows confocal images of hybrid cells formed by mouse macrophages phagocytosing the nuclei of tumor cells.

Exosomes are cell naturally secreting biomembrane vesicles with a diameter of about 30-140 nm. Firstly, the cell membranes usually invaginate and shed to form early endosomes. Then, the membranes of the early endosomes invaginate again under the regulation of the endosomal sorting complex required for transport (ESCRT) and related proteins in the cytoplasm, multiple nano-sized small vesicles are formed in the early endosomes in the form of endogenous budding, and the endosomes at this time are called multivesicular bodies (MVBs). Finally, the MVBs are fused with the cell membranes under the regulation of the RAB enzyme in the GTPase family to release the nanovesicles to the outside of the cells, and these small vesicles released to the outside of the cells are so called exosomes.

The secretion of exosomes is specific and can participate in the exchange of genetic information and signal communication between cells. Studies have demonstrated that the exosomes secreted by the DC "inherit" most of the surface molecules (such as MHC molecules, costimulatory molecules, etc.) of DC themselves. In recent years, exosomes of APCs, as more natural novel artificial nano APC systems, have been widely used in the field of tumor immunotherapy.

Compared with antigen-presenting cells, the extracellular nanovesicles of the antigen-presenting cells, i.e. exosomes, as therapeutic antitumor vaccines have the following advantages: (1) antigen-presenting cells are easily devitalized in vitro and need to be made and used on the spot, whereas exosomes are stable in structure with a long shelf life and can be preserved at −80° C. for more than 6 months; (2) antigen-presenting cells are easily to be induced by the tumor microenvironment to undergo phenotypic changes in the body (for example, changed into immunosuppressive M2 macrophages or DCregs) and lose the ability of activating T cells, whereas exosomes, as small-sized vesicles carrying inherent immune activation molecules that more stably, will not undergo transformation; (3) exosomes can be loaded with drugs for a chemotherapy or a photothennal therapy, so as to realize the combined treatment of an immunotherapy and other therapeutic methods; therefore, the exosomes based on antigen-presenting cells can be used to construct tumor vaccines with multiple functions.

The disclosure provides a hybrid cell formed by an antigen-presenting cell phagocytosing the nuclei of a tumor cell. Preferably, the antigen-presenting cell is dendritic cell, macrophage or B cell.

In a preferred embodiment of the disclosure, the antigen-presenting cells can phagocytose 1, 2, 3, 4, 5, 6 or more nuclei of tumor cells.

In a preferred embodiment of the disclosure, the tumor cells in the logarithmic growth phase are collected by centrifugation, resuspended in PBS, and washed twice; the cell pellets are resuspended and the cell suspension is processed and remove floc by cell strainer; and the sieved suspension is subjected to centrifugation and the lower pellets are nuclei.

Hybrid cells in the disclosure are prepared through the method of antigen-presenting cells (such as macrophages) endocytosing the nuclei of tumor cells, which is superior to the method of using macrophages to phagocytose tumor cells due to the fact that a variety of signal molecules (such as CD47, MHC-I molecule β chain, etc.) are liable to be expressed on the surfaces of the tumor cells, which causes macrophages to be unable to phagocytose the tumor cells, resulting in growth of the tumor cells together with the macrophages, even initiating the phenotypic changes of the macrophages, and subsequently promoting tumor cell growth.

Hybrid cells in the disclosure are prepared through the method of antigen-presenting cells (such as macrophages) endocytosing the nuclei of tumor cells. Compared with other modes of cell fusion, such as PEG fusion and electrofusion, the method used in the disclosure is more efficient, and the formation ratio of the hybrid cells can be as high as 100% without damaging cell viability. Generally, the cell fusion method has a very poor selectivity, which is liable to cause the fusion of macrophages with macrophages or the fusion of tumor cells with tumor cells, resulting in the appearance that a large number of fused cells are non-target products. Furthermore, either the PEG fusion or the electrofusion method will cause damage to cell viability, and the success rate of making macrophage-tumor hybrid cells that are finally viable is low, for example, is 10%-30%.

In a preferred embodiment of the disclosure, the hybrid cells are activated by an immunomodulator, such as lipopolysaccharide, monophosphoryl lipid A or unmethylated CpG oligodeoxynucleotide motif; the lipopolysaccharide and the like can further increase the expression levels of costimulatory factors and the tumor antigen-MHC I complex on the surfaces of the macrophages, and at the same time can facilitate the transformation of the macrophages into M1-type macrophages with antitumor effects. A large number of costimulatory molecules, tumor antigen-MHC I complexes and a variety of antitumor related signaling molecules for immune activation are carried on the surface of the hybrid exosomes secreted by such activated hybrid cells.

The disclosure also provides a method for preparing an exosome, comprising the steps of: extracting the nuclei from tumor cells, adding the nuclei of the tumor cells into a culture fluid of the antigen-presenting cell, incubating, then collecting a supernatant of the culture fluid, and performing differential centrifugation to collect the exosome.

In a preferred embodiment of the disclosure, the antigen-presenting cell phagocytoses the nuclei of the tumor cells to form a hybrid cell, and the hybrid cell secretes exosomes, which are hybrid exosomes.

In a preferred embodiment of the disclosure, the antigen-presenting cell as mentioned is dendritic cell, macrophage or B cell, and more preferably, the antigen-presenting cell is macrophage.

In a preferred embodiment of the disclosure, the endogenous expression of tumor antigens on a macrophage is successfully achieved through the strategy of the macrophage phagocytosing the nuclei of the tumor cells. In addition, the organelles of macrophages can be utilized by the nuclei of tumor cells to express tumor adhesion molecules, such adhesion factors can guide the exosomes to migrate to tumor sites, thereby solving the problem concerning the tumor targeting of the exosomes and providing a good premise for improving the tumor microenvironment.

In a preferred embodiment of the disclosure, an immunomodulator is added to the culture fluid of the antigen-presenting cells, and preferably, the immunomodulator is any one or a combination of at least two of lipopolysaccharide, monophosphoryl lipid A and unmethylated CpG oligodeoxynucleotide motif.

In a preferred embodiment of the disclosure, antigen-presenting cells such as macrophages having a strong phagocytic ability can be used to phagocytose the nuclei of tumor cells, the formed hybrid cells are stimulated with an immunomodulator such as lipopolysaccharide (LPS), and then exosomes are extracted from the resulting hybrid macrophages, thus obtaining an exosome-based vaccine formulation with the simulated functions of APC. Since the nuclei of tumor cells contains complete genetic information of the tumor cells, the nuclei of tumor cells after being endocytosed will utilize the organelles of macrophages to endogenously express the MHC I complex of tumor antigens on the macrophage membrane; the co-stimulation of LPS during the culture process can further increase the expression level of costimulatory factors and tumor antigen-MHC I complex on the surface of the macrophages, and at the same time can facilitate the transformation of the macrophages into M1-type macrophages with the antitumor effect. A large number of costimulatory molecules, tumor antigen-MHC I complexes and a variety of antitumor related signaling molecules for immune activation are carried on the surface of the hybrid exosomes secreted by such activated hybrid cells. These hybrid exosomes are similar to nano-scale APC; because of their nano-scale particle sizes, some exosomes can target lymph nodes and simulate the APC function in the lymph nodes by directly activating T cells and eliciting cellular immune response. In addition, since the hybrid exosomes carry certain tumor signals (such as adhesion molecules) which contribute to the homologous tumor targeting, some exosomes can be guided to the tumor sites through the directed chemotaxis of the homologous tumors. The hybrid exosomes within the tumors may rely on their immune activating internal signaling molecules to reversely transform the M2-type macrophages to M1-type macrophages, reduce the proportion of Tregs, and thus improve the tumor microenvironment.

In a preferred embodiment of the disclosure, the macrophages that have phagocytosed the nuclei of tumor cells successfully express E.G7 tumor antigen OVA, and moreover, the expression levels of T cell recognition signal MHC molecules, costimulatory factors, and M1-type macrophage marker molecule Ly-6C on the surface of the macrophages are upregulated; costimulatory molecules and T cell recognition signal MHC molecules are highly expressed on the surface of the exosomes, and high levels of cytokines for immune activation and a variety of chemokines are contained within the exosomes.

In a preferred embodiment of the disclosure, the exosomes of the disclosure have good dual targeting capabilities to lymph nodes and tumors; the lymph node-targeting is due to the nano-scale particle size of the exosomes, and the tumor-targeting ability is due to that the tumor signal molecules carried by the exosomes have homologous chemotaxis to the tumor sites.

In a preferred embodiment of the disclosure, a part of the exosomes targeting to the lymph nodes activate the APC by means of uptake by the APC, and then activate the proliferation of T lymphocytes; and other exosomes bind to the surface of T cells and directly activate the proliferation of T lymphocytes. About a quarter of the exosomes targeting to the tumor sites interact with tumor-associated macrophages to promote their transformation into M1-type macrophages; and meanwhile, the exosomes reduce the Treg infiltration in the tumor sites and increase the ratio of CTLs infiltration in the tumors, thereby effectively ameliorating the immunosuppressive tumor microenvironment.

In a preferred embodiment of the disclosure, the disclosure provides a pharmaceutical composition comprising the exosomes of the disclosure, in which the exosomes are suspended in a physiologically acceptable carrier which is, for example, a PBS buffer or physiological saline.

In a preferred embodiment of the disclosure, the disclosure provides a method for inhibiting tumor or cancer growth or progression in a subject in need thereof, comprising: administering an effective amount of the exosomes of the disclosure to the subject.

Preferably, the exosomes are administered by intravenous injection, intramuscular injection, subcutaneous injection, intrathecal injection or infusion and/or intra-organ infusion. For example, the exosomes are administered systemically in an amount of about $1.5\times10^{10}$ to about $1.5\times10^{13}$ exosome particles per kilogram of total body weight. In an alternative example, exosomes are administrated by injecting or infusing into a local tissue or an anatomical space in an amount of about $1.5\times10^{10}$ and $1.5\times10^{11}$ exosome particles. In certain other embodiments, the disclosure also comprises co-treatment of the subject using at least one additional anticancer agent.

The disclosure also provides a pharmaceutical composition comprising the hybrid cells or the exosomes as mentioned, and the pharmaceutical composition is, for example, an antitumor vaccine, which is used for the preventive or therapeutic treatment of the tumors and other diseases in a mammalian subject. The vaccine is easy and convenient to prepare, and meanwhile, it has universality applicable to the recurrence prevention, metastasis inhibition and treatment of any kind of tumors, and has a good antitumor effect.

The disclosure also provides a pharmaceutical composition comprising the exosomes as mentioned and a monoclonal antibody, which is, for example, a PD-1 antibody, a PD-L1 antibody, or a CTLA-4 antibody.

In a preferred embodiment of the disclosure, in vivo experimental results in mice demonstrate that the injection of the exosome vaccine of the disclosure does not cause tumorigenesis and damages to tissues and organs, and has good biological safety. In the investigation of the effects against in-situ tumor growth, it is found that the hybrid exosome vaccine has a good tumor inhibitory effects on E.G7 lymphoma and Muc1-B16 melanoma, significantly prolonging the survival time of mice. The use of the exosome vaccine of the disclosure in combination with PD-1 antibody shows a good preventive effect on the metastasis of Muc1-B16 melanoma cells in the lung, heart and kidney, and effectively prevents the in-situ recurrence and lung metastasis of Muc1-B16 melanoma after surgical resection.

One of the purposes of the disclosure also lies in a method for inducing a cytotoxic T cell response to tumor cells or tumors in a patient. This method comprises administering to the patient an effective amount of the exosomes of the disclosure, especially by intravenous injection or infusion, preferably by infusion. Especially, the purpose of the method is to induce the activation of dendritic cells and $CD8^+$ cytotoxic T cell response in the patient. As described above, specific $CD4^+$ helper T cell and $CD8^+$ cytotoxic T cell responses are achieved.

One of the purposes of the disclosure also lies in an anti-cancer treatment method of inducing the cytotoxic cell response to tumor cells or tumors as described above in a patient. This method comprises administering to the patient an effective amount of the exosomes of the disclosure, especially by intravenous injection or infusion, preferably by infusion.

In the disclosure, "effective amount" refers to an amount sufficient to produce a beneficial or desired result, such as a reduction in the rate of tumor or cancer progression. The effective amount can be administered in one or more administrations, applications or doses. The effective amount, that is, the appropriate dose, will vary depending on the body weight, age, health, disease or condition to be treated, and the route of administration. The dose of exosomes administered to a subject is an amount effective to achieve the desired beneficial therapeutic response in the subject's body over time.

Those skilled in the art will be able to easily determine the amount of inactivated exosomes to be administered by titrating the dose and the duration of administration to achieve the best clinical response, such as a reduction in the rate of cancer progression and/or spread rate, and/or an induction of the regression of cancer.

The pharmaceutical composition provided by the disclosure can be administered to a patient using the methods well known to those skilled in the art, such as intraarterial, intravenous and percutaneous injection, and intranasal, transbronchial, intramuscular or oral administration. The doses and the methods of administration will vary depending on the body weight and age of the patients and the method of administration, and can be chosen by those skilled in the art as needed.

The scope of the specific embodiments is disclosed herein, and these embodiments are only intended to illustrate several aspects of the disclosure.

Example 1. Preparation of E.G7-Macrophage Hybrid Cells (a) Nuclear Extraction Reagent (purchased from Solarbio) was used to extract nuclei from lymphoma cell E.G7-OVA (purchased from ATCC Cell Biology Collection):

E.G7-OVA cells were cultured in high-glucose 1640 medium (purchased from Gibco) containing 10% fetal bovine serum protein (purchased from Gibco), 1% penicillin-streptomycin (purchased from Gibco), 0.4 mg/mL G418 (purchased from Gibco), and 0.05 mM β-mercaptoethanol (purchased from Gibco). The cells were subjected to subculturing at a passage ratio of 1:5 every two days. The tumor cells in the logarithmic growth phase were collected by centrifugation, resuspended in PBS (Gibco), and washed twice. Cell pellets was resuspended in the Lysis buffer of the Nuclear Extraction Kit (purchased from Solarbio), and the cell density after resuspension is about $2\times10^7$/mL. Afterwards, 20 μL of Reagent A (purchased from Solarbio) was added to each milliliter of the cell suspension, pipetted repeatedly using a pipette to mix uniformly, and sieved through a 200-mesh sieve to remove floc. The sieved suspension was subjected to centrifugation at 700 g for 5 min, and the lower pellets were nuclei.

(b) 1.2 g of soluble starch (purchased from Xilong Chemical Co., Ltd.) was weighed, dissolved in 20 mL of sterile water, and heated until the solution was clear. The solution was added to a beaker containing 0.06 g of beef extract (purchased from Beijing Chemical Industry Group Co., Ltd.), 0.2 g of peptone (purchased from Beijing Chemical Works), and 0.1 g of sodium chloride (purchased from Beijing Chemical Works), and dissolved completely to prepare a 6% starch broth, which is used as a liquid for inducing the peritoneal macrophages in mice, and the starch broth was injected intraperitoneally in an amount of 1 mL in each C57 mouse (from Vital River Laboratory Animal Technology Co., Ltd.). Three days later, the mice were sacrificed by cervical dislocation, soaked in 75% alcohol (purchased from Beijing Chemical Works) for 5 min for sterilization, and 5 mL of PBS (purchased from Gibco) was injected into the abdominal cavity of the mice for lavage; the abdominal skin was cut open after gently rubbing the abdomen of the mice for several times, the peritoneum was exposed, the lavage fluid was aspirated with a syringe, the lavage fluid was collected and centrifuged at 1500 rpm for 5 min, and subjected to adherent culture for 12 h, the culture fluid was changed, the supernatant with cells suspended therein were discarded to obtain the remaining adherent cells, i.e. macrophages, and then an exosome-free DMEM complete medium was used to culture the macrophages, in which the component of the complete medium was exosome-free high-glucose DMEM medium (purchased from Gibco) containing 10% fetal bovine serum protein (purchased from Gibco) and 1% penicillin-streptomycin (purchased from Gibco); and DRAQ5 dye (purchased from Life Technologies) was used to stain the nuclei of the macrophages.

(c) The fresh E.G7-OVA tumor cell nuclei extracted in (a) were stained with 5 μg/mL DAPI solution (purchased from Beijing Fanbo Biochemicals Co., Ltd.), and then added to the exosome-free DMEM complete culture solution containing macrophages in (b) at a ratio of nuclei to macrophages of 2:1, so that the macrophages can endocytose the nuclei of the tumor cells to obtain tumor-macrophage hybrid cells comprising both the nuclei of macrophages themselves and the nuclei of E.G7-OVA, and then rhodamine-phalloidin dye (purchased from Life Technologies) was used to stain the cell membranes of the hybrid cells.

A laser scanning confocal microscope (Leica, SP5) was used to observe the hybrid cells at 405 nm, 561 nm and 633 nm; and as shown in FIG. 1, in addition to the nuclei of the macrophages, the prepared hybrid cells could also comprise different numbers of nuclei of E.G7-OVA tumor cells ranging from one to six, and the hybrid cells in which the macrophages phagocytosed one, two, three, four, and six nuclei of tumor cells were illustrated in order from left to right.

Example 2. Preparation of B16-Macrophage Hybrid Cells (a) Nuclear Extraction Reagent (purchased from Solarbio) was used to extract nuclei from melanoma cells Muc-B16 (purchased from ATCC Cell Biology Collection):

Muc1-B16 cells were subjected to adherent culture in a complete medium which is a 1640 medium (purchased from Gibco, without HEPES) containing fetal bovine serum protein (purchased from Gibco), 1% penicillin-streptomycin (purchased from Gibco), and 1 μg/mL puromycin (purchased from Gibco), and subculture at a ratio of 1:4 every 2-3 days. The logarithmic-phase cells were selected and collected by centrifugation, resuspended in PBS (purchased from Gibco), and washed twice. $2\times10^7$ cells were resuspended in 1 mL Lysis buffer of the Nuclear Extraction Kit (purchased from Solarbio), then 20 μL Reagent A (purchased from Solarbio) was added to each milliliter of the cell suspension, a 1 mL pipette head was used to pipette 10 times, 10 mL PBS (purchased from Gibco) was added to dilute the lysate immediately when the cell suspension became clear, centrifugation was carried out at 1400 r/min for 5 min, the lower pellets were resuspended and sieved to remove floc to obtain an Muc-B16 nucleus suspension with good dispersibility.

(b) 1.2 g of soluble starch (purchased from Xilong Chemical Co., Ltd.) was weighed, dissolved in 20 mL of sterile water, and heated until the solution was clear. The solution was added to a beaker containing 0.06 g of beef extract (purchased from Beijing Chemical Industry Group Co., Ltd.), 0.2 g of peptone (purchased from Beijing Chemical Works), and 0.1 g of sodium chloride (purchased from Beijing Chemical Works), and dissolved completely to prepare a 6% starch broth, which is used as a liquid for inducing the peritoneal macrophages in mice, and the starch broth was injected intraperitoneally in an amount of 1 mL in each C57 mouse (from Vital River Laboratory Animal Technology Co., Ltd.). Three days later, the mice were sacrificed by cervical dislocation, soaked in 75% alcohol (purchased from Beijing Chemical Works) for 5 min for sterilization, and 5 mL of PBS (Gibco) was injected into the abdominal cavity of the mice for lavage; the abdominal skin was cut open after gently rubbing the abdomen of the mice for several times, the peritoneum was exposed, the lavage fluid was aspirated with a syringe, the lavage fluid was collected and centrifuged at 1500 rpm for 5 min, and subjected to adherent culture for 12 h, the culture fluid was changed, the supernatant with cells suspended therein were discarded to obtain the remaining adherent cells, i.e. macrophages, and then an exosome-free DMEM complete medium was used to culture the macrophages, in which the component of the complete medium was exosome-free high-glucose DMEM medium (purchased from Gibco) containing 10% fetal bovine serum protein (purchased from Gibco) and 1% penicillin-streptomycin (purchased from Gibco).

(c) The fresh Muc1-B16 nuclei extracted in (a) were added to the exosome-free DMEM complete culture solution containing macrophages in (b) at a ratio of nuclei to macrophages of 2:1, so that the macrophages can endocytose the nuclei of the tumor cells to obtain tumor-macrophage hybrid cells comprising both the nuclei of macrophages themselves and the nuclei of Muc1-B16.

Example 3. Preparation of 4T1-Macrophage Hybrid Cells (a) Nuclear Extraction Reagent (purchased from Solarbio) was used to extract nuclei from breast cancer cell 4T1 (purchased from ATCC Cell Biology Collection):

4T1 cells were subjected to adherent culture, in which the complete medium was 1640 medium (purchased from Gibco, without HEPES) containing 10% fetal bovine serum protein (purchased from Gibco) and 1% penicillin-streptomycin (purchased from Gibco), and subculture at a ratio of 1:4 for every 2-3 days. The logarithmic-phase cells were selected and collected by centrifugation, resuspended in PBS (purchased from Gibco), and washed twice. $2\times10^7$ cells were resuspended in 1 mL Lysis buffer of the Nuclear Extraction Kit (purchased from Solarbio), then 20 μL Reagent A (purchased from Solarbio) was added to each milliliter of the cell suspension, a 1 mL pipette was used to pipette 10 times, 10 mL PBS (purchased from Gibco) was added to dilute the lysate immediately when the cell suspension became clear, centrifugation was carried out at 1400 r/min for 5 min, the lower pellets were resuspended and sieved to remove floc to obtain a 4T1 nucleus suspension with good dispersibility.

(b) 1.2 g of soluble starch (purchased from Xilong Chemical Co., Ltd.) was weighed, dissolved in 20 mL of sterile water, and heated until the solution was clear. The solution was added to a beaker containing 0.06 g of beef extract (purchased from Beijing Chemical Industry Group Co., Ltd.), 0.2 g of peptone (purchased from Beijing Chemical Works), and 0.1 g of sodium chloride (purchased from Beijing Chemical Works), and dissolved completely to prepare a 6% starch broth, which is used as a liquid for inducing the peritoneal macrophages in mice, and the starch broth was injected intraperitoneally in an amount of 1 mL in each Balbc mouse (from Vital River Laboratory Animal Technology Co., Ltd.). Three days later, the mice were sacrificed by cervical dislocation, soaked in 75% alcohol (purchased from Beijing Chemical Works) for 5 min for sterilization, and 5 mL of PBS (Gibco) was injected into the abdominal cavity of the mice for lavage; the abdominal skin was cut open after gently rubbing the abdomen of the mice for several times, the peritoneum was exposed, the lavage fluid was aspirated with a syringe, the lavage fluid was collected and centrifuged at 1500 rpm for 5 min, and subjected to adherent culture for 12 h, the culture fluid was changed, the supernatant with cells suspended therein were discarded to obtain the remaining adherent cells, i.e. macrophages, and then an exosome-free DMEM complete medium was used to culture the macrophages, in which the component of the complete medium was exosome-free high-glucose DMEM medium (purchased from Gibco) containing 10% fetal bovine serum protein (purchased from Gibco) and 1% penicillin-streptomycin (purchased from Gibco).

(c) The fresh 4T1 nuclei extracted in (a) were added to the exosome-free DMEM complete culture solution containing macrophages in (b) at a ratio of nuclei to macrophages of 2:1, so that the macrophages can endocytose the nuclei of the tumor cells to obtain tumor-macrophage hybrid cells comprising both the nuclei of macrophages themselves and the nuclei of 4T1.

Example 4. Preparation of Human-Derived A375-Macrophage Hybrid Cells (a) Nuclear Extraction Reagent (purchased from Solarbio) was used to extract nuclei from human-derived melanoma cells A375 (purchased from ATCC cell bank):

A375 cells were subjected to adherent culture, in which the complete medium was a DMEM medium (purchased from Gibco, without HEPES) containing fetal bovine serum protein (purchased from Gibco) and 1% penicillin-streptomycin (purchased from Gibco), and subculture at a ratio of 1:4 for every 2-3 days. The logarithmic-phase cells were selected and collected by centrifugation, resuspended in PBS (purchased from Gibco), and washed twice. $2\times10^7$ cells were resuspended in 1 mL Lysis buffer of the Nuclear Extraction Kit (purchased from Solarbio), then 20 μL Reagent A (purchased from Solarbio) was added to each milliliter of the cell suspension, a 1 mL pipette head was used to pipette 10 times, 10 mL PBS (purchased from Gibco) was added to dilute the lysate immediately when the cell suspension became clear, centrifugation was carried out at 1400 r/min for 5 min, the lower pellets were resuspended and sieved to remove floc to obtain A375 nucleus suspension with good dispersibility.

(b) A sterile blood collection needle was used to collect 50 mL of peripheral blood from a healthy human by means of venous blood collection, and a lymphocyte separation solution was used to extract lymphocytes: the peripheral blood from human was diluted with an HBSS solution at a ratio of 1:1 and added along the wall of the centrifuge tube to a density gradient separation solution having a volume equal to that of the peripheral blood, centrifugation was carried out at 2000 rpm for 15 min, the second layer (the white layer) comprising lymphocytes was collected and washed by adding an HBSS solution with 10 times volume of the lymphocyte suspension, then centrifuged at 1500 rpm for 10 min, washed twice, and resuspended with HBSS; then a human CD14 magnetic bead sorting kit (purchased from Miltenyi) was used to sort and extract mononuclear cells by operating according to the instructions, then the mononuclear cells were cultured using a 1640 complete medium containing 500 U/mL human colony stimulation factor (purchased from Invitrogen), and human-derived macrophages were obtained after 3-5 days.

(c) The fresh A375 nuclei extracted in (a) were added to the exosome-free 1640 complete culture solution containing human-derived macrophages in (b) at a ratio of nuclei to macrophages of 2:1, so that the macrophages can endocytose the nuclei of the tumor cells to obtain human-derived tumor-macrophage hybrid cells comprising both the nuclei of macrophages themselves and the nuclei of A375.

Example 5. Preparation of Exosomes Derived from E.G7-Macrophage Hybrid Cells The hybrid cells that were not stained with any fluorescent dye in Example 1 were cultured, the nuclei of tumor cells were added, 4 days later the culture supernatant of the hybrid cells was collected and centrifuged at 300 g for 10 min to remove residual cell pellets; the supernatant was taken out and centrifuged again at 2,000 g for 10 min to remove the dead cell pellets; the resultant supernatant was taken out and centrifuged again at 10,000 g for 30 min to remove the cell debris pellets; and finally, the generated supernatant was taken out and centrifuged at 120,000 g for 2 hours to remove the final supernatant, and PBS (purchased from Gibco) was used to resuspend the final pellets to obtain an exosome suspension.

Example 6. Characterization of Exosomes Derived from E.G7-Macrophage Hybrid Cells The fresh exosomes in Example 5 extracted by ultracentrifugation were mixed with an equal amount of 4% paraformaldehyde solution, that is, the exosomes were suspended in 2% paraformaldehyde solution and fixed for 30 min. then 10 μL exosome suspension was dropped on parafilm, a TEM copper grid was covered on the droplet to ensure that the side of plating layer was in contact with the droplets, and the copper grid was allowed to adsorb the droplets on the film for 10 min at room temperature. Then, the copper grid was carefully removed with tweezer, the residual droplets on the copper grid were absorbed with a filter paper, and the copper grid was washed twice on the PBS droplets added to parafilm in advance for 5 min each time. Then the copper grid was removed and the residual liquid on the copper grid was absorbed with a filter paper. Afterwards, the copper grid was transferred to 50 μL of uranyl acetate droplets and counterstained for 30 s, then the copper grid was removed and the residual uranyl acetate liquid on the copper grid was gently absorbed with a filter paper, and the side of the plating layer of the copper grid was allowed to face upwards and be dried in the air for 10 min. Afterwards, the air-dried copper grid was observed under a 120 kV biological transmission electron microscope, and the result was shown in FIG. 2. The stock solution of the exosomes extracted by ultracentrifugation was diluted 500-2000 times with PBS, 1 mL of the exosome dilution was injected into the injection port of a nanoparticle tracking analyzer using a syringe, the number of exosomes in the dilution was calculated through the detection and analysis of the system, and the particle size distribution diagram of the exosomes was obtained as shown in FIG. 3. Wes full-automatic protein expression analysis system was used to detect the various proteins in exosomes. Firstly, a biotinylated standard sample ladder was prepared, and a sample for loading was prepared by mixing the exosomes having the same protein concentration with ⅕ volume of Fluorescent Master Mix uniformly. The ladder and the sample were heated at 95° C. for 5 min for protein denaturation. Afterwards, the ladder and the sample were added respectively to the corresponding sample wells of the microtiter plate, and dilutions of the primary antibodies against CD9, CD86, MHC I and MHC II were added to the corresponding primary antibody wells of the microtiter plate; HRP-secondary antibody dilutions corresponding to different primary antibody sources were added to the lower row of wells; and Luminol-Peroxide mixtures were added to the bottommost row of wells. Afterwards, a capillary injector was installed on the analyzer, the microtiter plate was placed under the injector, the analyzer was turned on for performing detection and analysis, and the experimental results were shown in FIG. 4.

Figure 2:
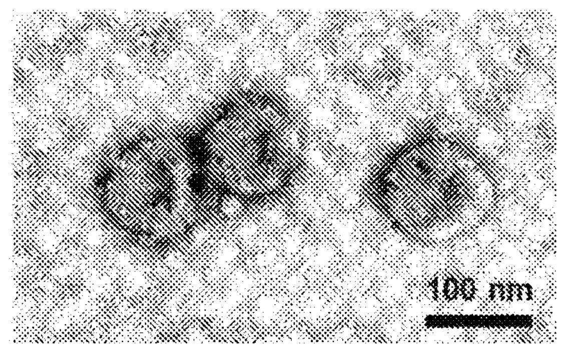
FIG. 2 shows a transmission electron microscope image of mouse-derived exosomes of the disclosure.
Figure 3:
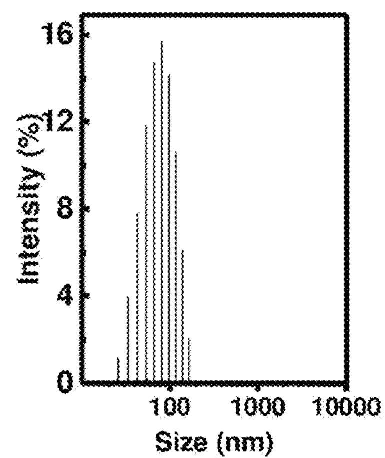
FIG. 3 shows a particle size distribution diagram of mouse-derived exosomes of the disclosure.
Figure 4:
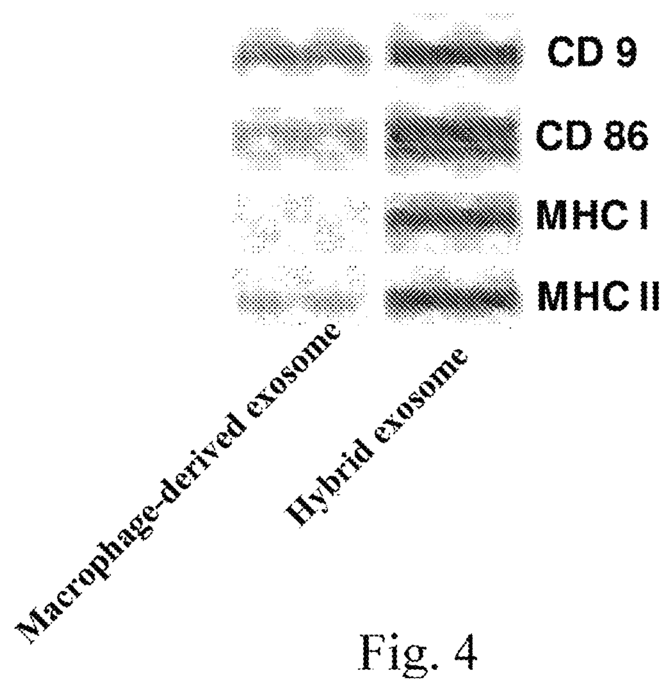
FIG. 4 shows an expression profile of four protein molecules (exosomal marker protein CD9, costimulatory molecule CD86, major histocompatibility complex I, major histocompatibility complex II) on the mouse-derived exosomes of the disclosure.

It can be seen from FIG. 2 that the prepared exosomes had a classic cup-shaped structure; the particle size distribution diagram in FIG. 3 showed that the average particle size of the exosomes was 90 nm; the western blotting result in FIG. 4 showed that there was expression of exosome marker protein CD9 on the surfaces of both the macrophage-derived exosomes and the exosomes of the disclosure; as compared with the simple macrophage-derived exosomes, the gray scale values of the blotting of costimulatory molecule CD86, histocompatibility complex I, and histocompatibility complex II on the same amount of the exosomes of the disclosure were higher, indicating that the expression amounts of these three proteins were increased.

Example 7. Preparation of Exosomes Derived from B16-Macrophage Hybrid Cells

The hybrid cells in Example 2 were stimulated with a lipopolysaccharide (purchased from Sigma) having a final concentration of 1 μg/mL, 4 days later the culture supernatant of the hybrid cells was collected and centrifuged at 300 g for 10 min to remove residual cell pellets; the supernatant was taken out and centrifuged again at 2,000 g for 10 min to remove the dead cell pellets; the resultant supernatant was taken out and centrifuged again at 10,000 g for 30 min to remove the cell debris pellets; and finally, the generated supernatant was taken out and centrifuged at 120,000 g for 2 hours to remove the final supernatant, and PBS (purchased from Gibco) was used to resuspend the final pellets to obtain the exosome suspension of the disclosure.

Example 8. Preparation of Exosomes Derived from 4T1-Macrophage Hybrid Cells

The hybrid cells in Example 3 were stimulated with a lipopolysaccharide (purchased from Sigma) having a final concentration of 1 μg/mL, 4 days later the culture supernatant of the hybrid cells was collected and centrifuged at 300 g for 10 min to remove residual cell pellets; the supernatant was taken out and centrifuged again at 2,000 g for 10 min to remove the dead cell pellets; the resultant supernatant was taken out and centrifuged again at 10,000 g for 30 min to remove the cell debris pellets; and finally, the generated supernatant was taken out and centrifuged again at 120,000 g for 2 hours to remove the final supernatant, and PBS (purchased from Gibco) was used to resuspend the final pellets to obtain the exosome suspension of the disclosure.

Example 9. Preparation of Exosomes Derived from Human-Derived A375-Macrophage Hybrid Cells The hybrid cells in Example 4 were stimulated with a lipopolysaccharide (purchased from Sigma) having a final concentration of 1 μg/mL, 4 days later the culture supernatant of the hybrid cells was collected and centrifuged at 300 g for 10 min to remove residual cell pellets; the supernatant was taken out and centrifuged again at 2,000 g for 10 min to remove the dead cell pellets; the resultant supernatant was taken out and centrifuged again at 10,000 g for 30 min to remove the cell debris pellets; and finally, the generated supernatant was taken out and centrifuged at 120,000 g for 2 hours to remove the final supernatant, and PBS (purchased from Gibco) was used to resuspend the final pellets to obtain the human-derived exosome (h-nc-lps-exo) suspension of the disclosure.

Example 10. Characterization of Exosomes Derived from Human-Derived A375-Macrophage Hybrid Cells of the Disclosure The fresh human-derived exosomes in Example 9 extracted by ultracentrifugation were mixed with an equal amount of 4% paraformaldehyde solution, that is, the exosomes were suspended in 2% paraformaldehyde solution and fixed for 30 min. Afterwards, 10 μL exosome suspension was dropped on parafilm, a copper grid was covered on the droplets to ensure that the side of plating layer was in contact with the droplets, and the copper grid was allowed to adsorb the droplets on the film for 10 min at room temperature. Then, the copper grid was carefully removed with tweezer, the residual droplets on the copper grid were absorbed with a filter paper, and the copper grid was washed twice on the PBS droplets added to parafilm in advance for 5 min each time. Then the copper grid was removed and the residual liquid on the copper grid was absorbed with a filter paper. Afterwards, the copper grid was transferred to 50 μL of uranyl acetate droplets and counterstained for 30 s, then the copper grid was removed and the residual uranyl acetate liquid on the copper grid was gently absorbed with a filter paper, and the side of the plating layer of the copper grid was allowed to face upwards and be dried in the air for 10 min. The air-dried copper grid was observed under a 120 kV biological transmission electron microscope, and the result was shown in FIG. 5.

Figure 6:
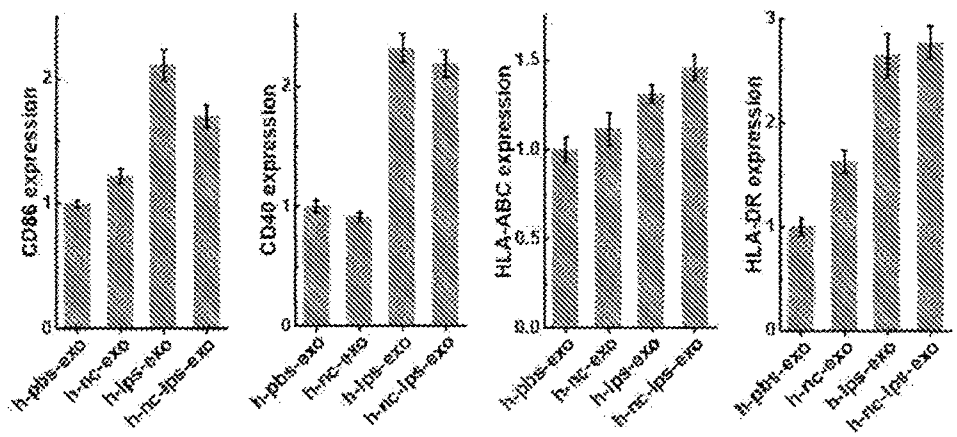
FIG. 6 shows expression profiles of four protein molecules (CD86, CD40, HLA-ABC, and HLA-DR) on the human-derived exosomes of the disclosure.

The human-derived hybrid exosomes (h-nc-lps-exo) in Example 9 were incubated with an anti-human CD9 antibody-coupled magnetic beads (purchased from Thermo Fisher), then the magnetic beads bound with the exosomes were separated with a magnetic separation rack and washed to obtain a suspension, after that, the exosome-magnetic bead suspension was labeled in the dark with 0.25 μg PE-labeled anti-CD86, 0.25 μg PE-labeled anti-CD40, 0.25 μg FITC-labeled anti-HLA-ABC, and 0.25 μg BV510-labeled anti-HLA-DR fluorescent antibody (all purchased from ebioscience) for 25 min (4° C., and then the magnetic beads bound with dye-exosomes were separated with a magnetic separation rack, washed and resuspended in PBS followed by detecting by using a flow cytometer. At the same time, the following control groups were set up: a group of untreated human-derived macrophage-derived exosomes (h-pbs-exo), a group of the exosomes in Example 9 without lipopolysaccharide stimulation (h-nc-exo), and a group of human-derived macrophage-derived exosomes only stimulated by a lipopolysaccharide (h-lps-exo); detection was performed as the above steps, and the detection results were shown in FIG. 6.

Figure 5:
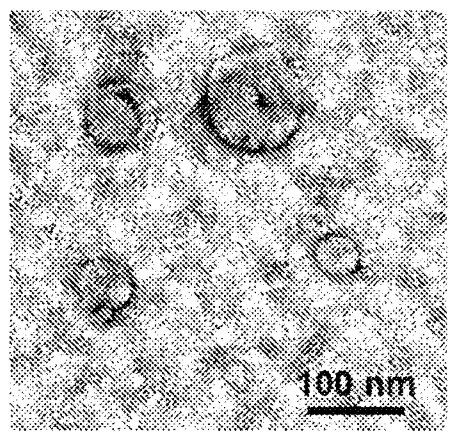
FIG. 5 shows a transmission electron microscope image of human-derived exosomes of the disclosure.

It can be seen from FIG. 5 that the prepared human-derived exosomes h-nc-lps-exo had a classic cup-shaped structure. It can be seen from FIG. 6 that h-lps-exo and h-nc-lps-exo comprised significantly more costimulatory molecules CD86 and CD40 as compared with h-pbs-exo and h-nc-exo; and the expression amounts of the type I major histocompatibility complex molecules (HLA-ABC) and type II major histocompatibility complex molecules (HLA-DR) related to antigen presentation on h-nc-lps-exo were slightly higher as compared with those on h-lps-exo, and the enrichment of such activation signal molecules was beneficial for the exosomes to exert a more effective immune activation response in vivo.

Example 11. Dual Targeting of Mouse-Derived Exosomes of the Disclosure to Lymph Nodes and Tumors 100 μL of exosomes were labeled using 1 μM near-infrared fluorescent lipophilic dye DiR (purchased from Beijing Fanbo Biochemicals Co., Ltd.) and incubated at 37° C. for 1 h, then the exosomes of the disclosure prepared in Example 5 were added dropwise onto the upper side of a gel filtration column (purchased from Thermo Scientific), and centrifugation was carried out at 700 g for 2 min, in which the free dye was retained inside the gel column and the liquid of the lower layer was the DiR-labeled hybrid exosome solution. $3.7 \cdot 10^9$ DiR-exosomes were injected subcutaneously into the back of C57BL/6 mice (from Vital River Laboratory Animal Technology Co., Ltd.), then the mice were anesthetized at different times within 96 hours, the situations of distribution of DiR-hybrid exosomes in the body of the mice were observed at 750 nm using an animal in-vivo imaging system, and the changes of the fluorescence signals in the lymph nodes and tumor sites at different times were analyzed. The experimental results were shown in FIG. 7 and FIG. 8. In addition, the mice were dissected at 48 h; the inguinal and axillary lymph nodes, tumor, heart, liver, spleen, lung, and kidney were taken out separately and the fluorescence signals in them were detected using a small animal in-vivo imaging system; and the experimental results were shown in FIG. 9.

Figure 7:
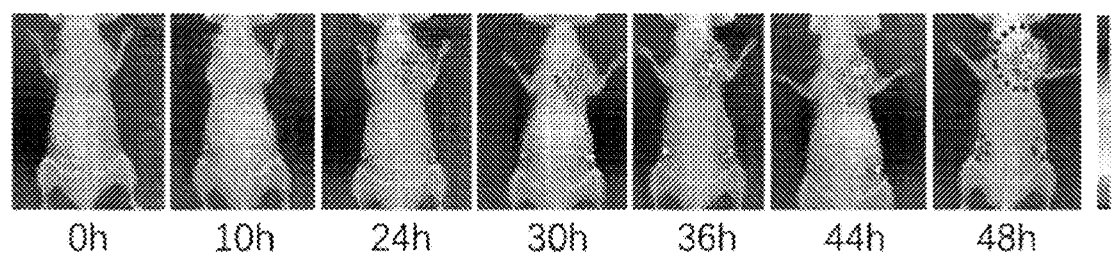
FIG. 7 shows enrichment of the mouse-derived exosomes of the disclosure in mouse lymph nodes and tumors after subcutaneous injection.
Figure 8:
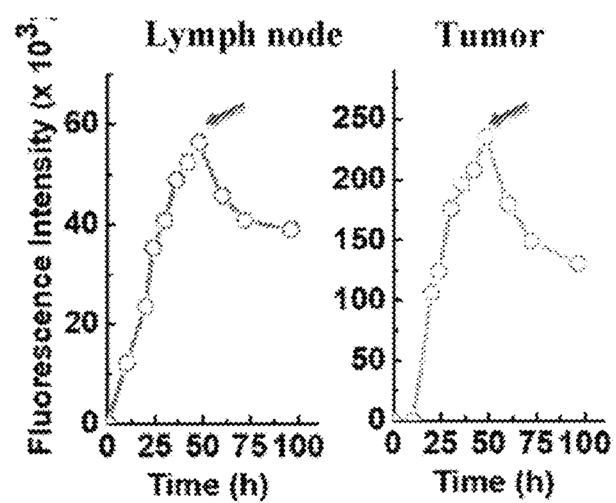
FIG. 8 shows targeting kinetic curves of the mouse-derived exosomes of the disclosure in mouse lymph nodes and tumor sites.
Figure 9:
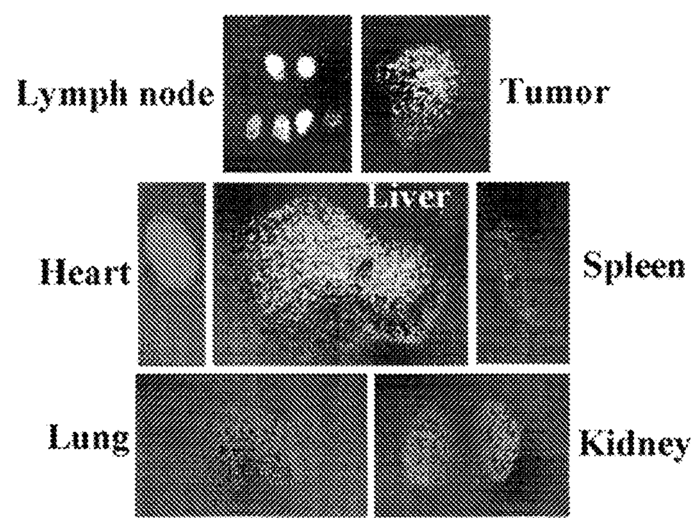
FIG. 9 shows enrichment of the signals of the mouse-derived exosomes of the disclosure in different tissues of mouse 48 hours after injection.

It can be seen from FIG. 7 that the fluorescence signals of exosomes were gradually enriched in the inguinal lymph nodes and tumors (indicated by the dotted line) over time. FIG. 8 showed the quantitative data for the changes of the fluorescence signals over time in the inguinal lymph nodes and tumor sites in mice, it can be seen from this figure that the fluorescence signals in the lymph nodes and tumor site were gradually enhanced over time during the first 48 hours after the subcutaneous injection of exosomes, and reached a peak at 48 h, and then the fluorescence signals in both sites were attenuated over time. It can be seen from FIG. 9 that there were strong fluorescence signals in the inguinal and axillary lymph nodes and tumor tissue in the mice; however, as for the various organs of the mice, except for the inevitable fluorescence enrichment in the liver, the fluorescence signals were not obvious in other organs, indicating that the exosomes of the disclosure administered by subcutaneous injection did have good capabilities of targeting to lymph nodes and tumors dually.

Example 12. Types of Cells Interacting with the Mouse-Derived Exosomes of the Disclosure in Lymph Nodes The exosomes of the disclosure prepared in Example 5 were fluorescently labeled using the method in Example 11 to obtain DiR-labeled exosomes. $3.7\times10^9$ DiR-exosomes were injected subcutaneously into the back of C57BL/6 mice (purchased from Vital River Laboratory Animal Technology Co., Ltd.), the mice were sacrificed at 48 h, the lymph nodes were taken out and ground to obtain a single cell suspension, and then the single cell suspension was labeled in the dark for 25 min (4° C.) using 0.25 μg of Pacific Blue-labeled anti-F4/80, 0.25 μg of Alex Fluro700-labeled anti-CD11b, 0.25 μg of Alex Fluro 488-labeled anti-CD11c, 0.25 μg of BV605-labeled anti-MHC II, 0.25 μg of BV510-labeled anti-CD3, 0.25 μg of APC-labeled anti-CD4, and 0.25 μg of PE-labeled anti-CD8 fluorescent antibodies, respectively (all of the fluorescent antibodies were purchased from ebioscience). The cells were washed twice with 500 μL Stain buffer (purchased from ebioscience), then the cells were resuspended and detected using a flow cytometer to analyze the proportions of four cell types, i.e., the macrophages ($F4/80^+CD11b^+$), the dendritic cells ($CD11c^+$ MHC $II^+$), the CD4 T cells ($CD3^+CD4^+$), and the CD8 T cells ($CD3^+CD8^+$) in the DiR signal positive cell population, in which 500,000 cells were collected for each sample for analysis and the results were shown in FIG. 10.

Figure 10:
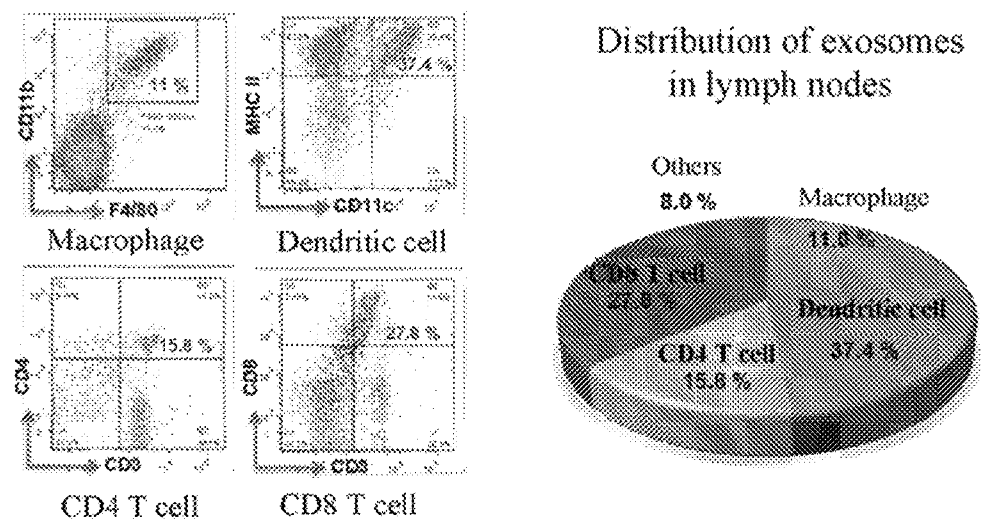
FIG. 10 shows flow cytometry analysis images and a pie chart of different immune cells interacted with the mouse-derived exosomes of the disclosure in lymph nodes.

As can be seen from FIG. 10, among the DiR-positive cell population, 11% were F4/80 and CD11b double positive myeloid-derived macrophages, 37.4% were CD11c and MHC II double positive dendritic cells, 15.8% were CD4 T cells, and 27.8% were CD8 T cells. The proportions of various cells were displayed in a pie chart, and it can be seen that the antigen-presenting cells (macrophages and dendritic cells) and T cells (CD4 and CD8) accounted for a proportion of 92%, indicating that most of the DiR-labeled exosomes interacted with the antigen-presenting cells or T cells after they entered the lymph nodes, and the APCs, as helper cells for the immune response, will also subsequently interact with T cells to transmit immune activation signals.

Example 13. T Cell Immune Activation Effects of Mouse-Derived Exosomes of the Disclosure The situation of the proliferation of T cells was investigated by a fluorescent labeling method using carboxyfluorescein diacetate succinimidyl ester (CFSE). The basic principle is as follows: CFSE is a cell stain that can fluorescently label living cells, CFSE after entering cells can irreversibly bind to the amino groups in the cells and couple to the cell proteins; CFSE-labeled fluorescence can be evenly distributed to the two daughter cells in the process of cell division and proliferation, resulting in the fluorescence intensity in the daughter cells being half that of the parent cell; and the fluorescence intensity can be analyzed by a flow cytometer at 488 nm excitation light to quickly and accurately detect the situation of the proliferation of the lymphocytes.

(a) The macrophages/dendritic cells stimulated for 72 h by the hybrid exosomes of the disclosure prepared from the hybrid cells prepared in Example 5 were co-incubated with CFSE-stained spleen cells to detect the T cell proliferation effects. The specific experimental steps were as follows: 1. staining of spleen cells: the spleen cells of C57BL/6 mice were stained with CFSE (purchased from Life Technologies) having a working concentration of 0.5 μM for 7 min (37° q, staining was stopped using 4 times volume of cold fetal bovine sera, the resultant cells were placed in an ice bath for 5 min, and centrifuged, and the cells were resuspended using a fresh 1640 complete medium and washed twice; 2. pretreatment of 96-well plates: 96-well plates were pretreated in advance with 1 μg/mL CD3 solution (purchased from ebioscience) overnight at 4° Q the CD3 solution was removed on the second day and the plates were washed twice with PBS (purchased from Gibco) for ready to use; 3. cell co-incubation: the T cells after cell counting were co-incubated with the macrophages/dendritic cells stimulated with the hybrid exosomes at a ratio of 1:2, and the cells were collected after a certain period of time; 4. staining and detection by flow cytometry: the cells were stained using 0.25 μg of BV510-labeled anti-CD3, 0.25 μg of eF450-labeled anti-CD4, and 0.25 μg of PE-labeled anti-CD8 antibodies (all of the antibodies for flow cytometry were from ebioscience), and the situations of the division and proliferation of the $CD3^+CD8^+$ T cells and the $CD3^+$ $CD4^+$ T cells were detected using a flow cytometer. For each sample, 10,000 cells were collected for analysis, and the results were shown in FIG. 11 and FIG. 12.

Figure 13:
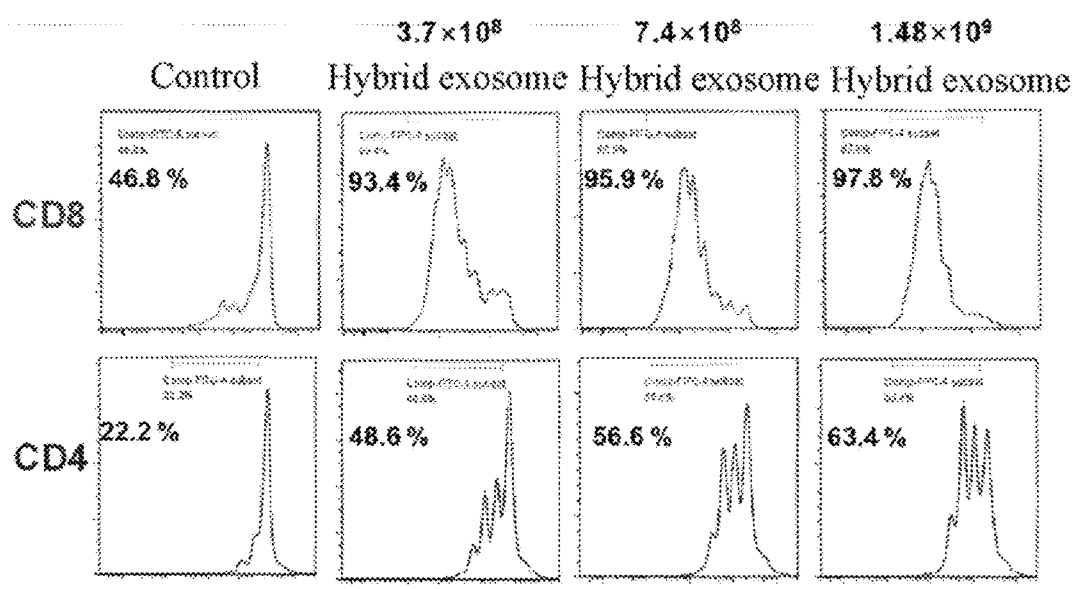
FIG. 13 shows proliferation effects of T cells after being directly activated by the mouse-derived exosomes of the disclosure.

(b) Different concentrations of the exosomes were co-incubated with the CFSE-stained T cells to detect the T cell proliferation effects. The specific experimental steps were as follows: 1. staining of spleen cells: the spleen cells of C57BL/6 mice were taken and stained with CFSE (purchased from Life Technologies) having a working concentration of 0.5 μM for 7 min (37° C.), staining was stopped using 4 times volume of cold fetal bovine sera, the resultant cells were placed in an ice bath for 5 min, and centrifuged, and the cells were resuspended in a fresh medium and washed twice. 2. Pretreatment of 96-well plates: 96-well plates were pretreated in advance with 1 μg/mL CD3 (purchased from ebioscience) solution overnight at 4° C., the CD3 solution was removed on the second day and the plates were washed twice with PBS (purchased from Gibco) for ready to use. 3. Co-incubation of exosomes and T cells: the CFSE-T cells were inoculated in a 96-well plate, and then different doses of hybrid exosomes were added for co-incubation, and the cells were collected after a certain period of time. 4. Staining and detection by flow cytometry: the cells were stained using BV510-labeled anti-CD3, eF450-labeled anti-CD4, and PE-labeled anti-CD8 antibodies (all of the antibodies for flow cytometry were purchased from ebioscience), and the situations of the division and proliferation of the $CD3^+CD8^+$ T cells and the $CD3^+CD4^+$ T cells were detected using a flow cytometer. For each sample, 10,000 cells were collected for analysis. The results were shown in FIG. 13.

Figure 11:
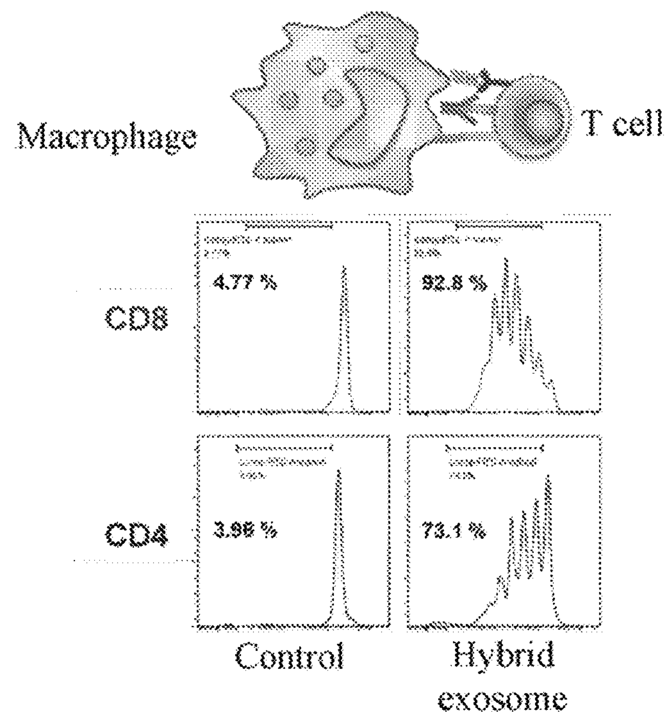
FIG. 11 shows a schematic diagram of interaction between a macrophage activated by the mouse-derived exosomes of the disclosure and a T cell, and shows the corresponding T cell proliferation effects.
Figure 12:
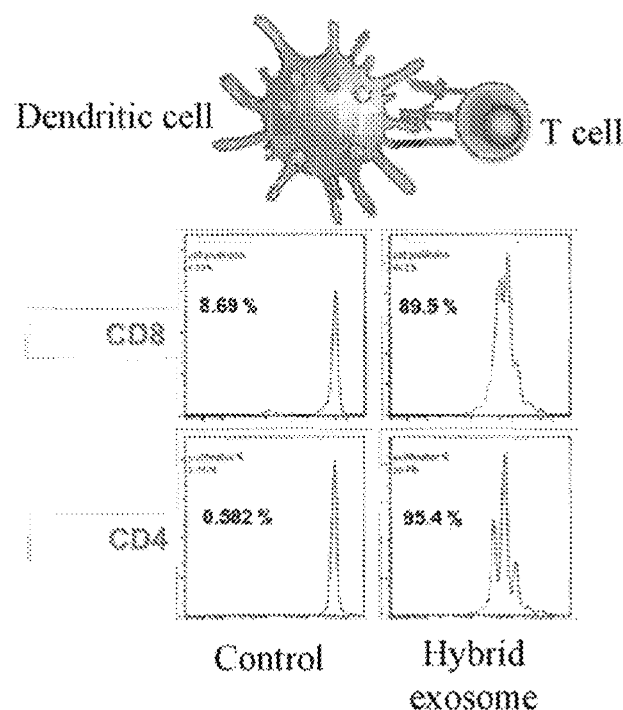
FIG. 12 shows a schematic diagram of interaction between a dendritic cell activated by the mouse-derived exosomes of the disclosure and a T cell, and shows the corresponding T cell proliferation effects.

It can be seen from FIG. 11 and FIG. 12 that both the macrophages and the dendritic cells activated by the hybrid exosomes of the disclosure prepared from the hybrid cells can initiate the obvious proliferation of the CD8 T cells and the CD4 T cells, indicating that the exosomes can further activate the T cells in the lymph nodes by means of activating the antigen-presenting cell (such as macrophages and dendritic cells). It be seen from FIG. 13 that, as compared with the control group, the proliferation rates of the CD8 T cells and the CD4 T cells in high-dose ($1.48\times10^9$) exosome group were increased by 40%-50%, and the exosomes can also produce a strong effect of proliferating CD8 T cells even under the stimulation at a low concentration ($3.7\times10^{8}$), demonstrating that the exosomes can directly interact with the T cells in the lymph nodes and thus activate T cell proliferation.

Example 14. T Cell Immune Activation Effects of Human-Derived Exosomes of the Disclosure The human-derived exosomes in Example 9 were co-incubated with the CFSE-stained human-derived T cells to detect the human-derived T cell proliferation effects. The specific experimental steps were as follows: 1. staining of human peripheral blood T cells: peripheral blood was collected from a healthy human, the lymphocytes were separated from the peripheral blood using a human lymphocyte separation solution, then Pan T sorting magnetic beads (purchased from Miltenyi) were used and operated according to the instructions to separate the human-derived T cells, then the cells were stained with CFSE (purchased from Life Technologies) having a working concentration of 0.5 μM for 7 min (37° C.), staining was stopped using 4 times volume of cold fetal bovine sera, the resultant cells were placed in an ice bath for 5 min, and centrifuged, and the cells were resuspended in a fresh medium and washed twice. 2. pretreatment of 96-well plates: 96-well plates were pretreated in advance with 1 μg/mL of an anti-human CD3 antibody (purchased from ebioscience) solution overnight at 4° C., the anti-CD3 antibody solution was removed on the second day and the plates were washed twice with PBS (purchased from Gibco) for ready to use. 3. co-incubation of exosomes and T cells: the CFSE-T cells were inoculated in a 96-well plate, and then different doses of human-derived hybrid exosomes were added for co-incubation, and the cells were collected after a certain period of time. 4. staining and detection by flow cytometry: the human T cells were stained using Super Bright600-labeled anti-CD3, APC-labeled anti-CD4, and AF700-labeled anti-CD8 antibodies (all of the antibodies for flow cytometry were purchased from ebioscience), and the situations of the division and proliferation of the $CD3^{+}CD8^{+}$ T cells and the $CD3^{+}CD4^{+}$ T cells were detected using a flow cytometer. For each sample, 10,000 cells were collected for analysis. The results were shown in FIG. 14.

Figure 14:
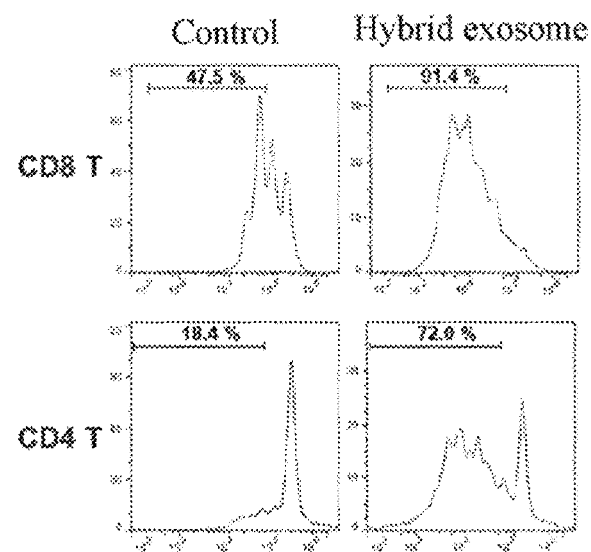
FIG. 14 shows proliferation effects of human T cells after being directly activated by the human-derived exosomes of the disclosure.

It can be seen from FIG. 14 that the exosomes of the disclosure prepared from human hybrid cells can directly initiate the massive proliferation of human-derived CD8 T cells and CD4 T cells simultaneously, and have strong immune activation effects.

Example 15. The Tumor Killing Ability of T Cells Activated by the Human-Derived Exosomes of the Disclosure The human-derived exosomes in Example 9 were co-incubated with human-derived T cells, then the proliferated human-derived T cells were co-cultured with A375 tumor cells, and an LDH kit (purchased from Beyotime) was used to examine the tumor cell-killing effects. The specific experimental steps were as follows: 1. separation of human peripheral blood T cells: peripheral blood was collected from a healthy human, the lymphocytes were separated from the peripheral blood using a human lymphocyte separation solution, and then Pan T sorting magnetic beads (purchased from Miltenyi) were used and operated according to the instructions to separate the human-derived T cells. 2. pretreatment of 96-well plates: 96-well plates were pretreated in advance with 1 μg/mL of an anti-human CD3 antibody (purchased from ebioscience) solution overnight at 4° C., the anti-CD3 antibody solution was removed on the second day and the plates were washed twice with PBS (purchased from Gibco) for ready to use. 3. co-incubation of exosomes and T cells: the T cells were inoculated in a 96-well plate, and then different doses of the human-derived hybrid exosomes were added for co-incubation, and the T cells were collected after a certain period of time. 4. co-culture of T cells and A375 cells: the T cells and A375 cells were mixed at ratios of 2.5:1, 5:1, and 15:1 (E:T), respectively, and inoculated in a new 96-well plate for co-culture for 24 h, a CCK8 kit was used and operated according to the instructions, and a microplate reader was used to detect the OD values at 450 nm, the tumor cell-killing rates were calculated, and the results were shown in FIG. 15.

Figure 15:
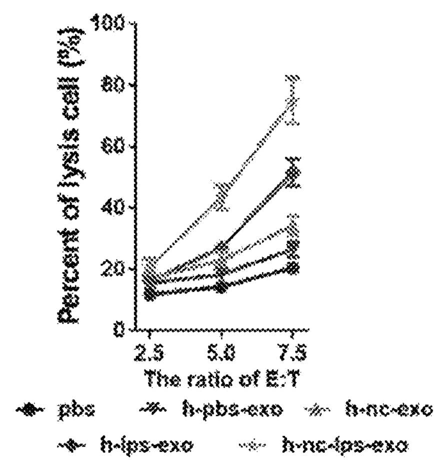
FIG. 15 shows tumor cell-killing effects of human T cells activated by the human-derived exosomes of the disclosure.

It can be seen from FIG. 15 that, as compared with multiple control groups, the group of the exosomes of the disclosure (h-nc-lps-exo) had the highest tumor cell-killing efficiency, and the tumor killing efficiency was positively correlated to the ratio of the effector T cells to the tumor cells, indicating that the exosomes of the disclosure can activate the massive proliferation of T cells, and these T cells can effectively recognize and kill tumor cells.

Example 16. Types of Cells Interacting with the Exosomes of the Disclosure in Tumor (a) Establishment of E.G7 lymphoma model: 6-8 weeks old male C57BL/6 mice (purchased from Vital River Laboratory Animal Technology Co., Ltd.) were selected, and $5\times10^{5}$ of E.G7 lymphoma cells (purchased from ATCC cell bank) were subcutaneously injected into the left axillary sites of the mice to construct an E.G7 lymphoma model.

(b) The hybrid exosomes in Example 5 prepared from the hybrid cells were fluorescently labeled by the method in Example 11 to obtain DiR (purchased from Beijing Fanbo Biochemicals Co., Ltd.) labeled hybrid exosomes. DiR-hybrid exosomes were intratumorally injected into the E.G7 tumors in C57BL/6 mice (purchased from Vital River Laboratory Animal Technology Co., Ltd.), the mice were sacrificed 48 hours later and the tumor tissues were taken out and ground, followed by lysing red blood cells and washing, and a single cell suspension was obtained. Then the single cell suspension was labeled in the dark for 25 min (4°) using 0.25 μg of Pacific Blue-labeled anti-F4/80 and 0.25 μg of Alex Fluro 700-labeled anti-CD11b (both purchased from ebioscience). The cells were resuspended after washing twice with the Stain buffer (purchased from eboscience) and detected using a flow cytometer to analyze the proportion of the cell type of macrophages ($F4/80^{+}CD11b^{+}$) in the DiR signal positive cell population, in which 500,000 cells were collected for each sample for analysis. The experimental results were shown in FIG. 16.

Figure 16:
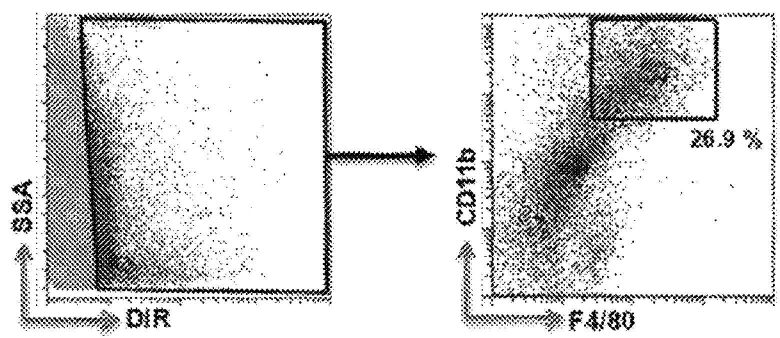
FIG. 16 shows the proportion of hybrid exosomes interacting with macrophages after the intratumoral injection of the mouse-derived exosomes of the disclosure.

It can be seen from FIG. 16 that, among the various types of DiR-hybrid exosome-positive cells in the tumor cell suspension, $CD11b^{+}F4/80^{+}$ double-positive macrophages accounted for 26.9%, meaning that more than 1/4 of the exosomes injected intratumorally interacted with the tumor-associated macrophages in the tumor.

Example 17. Effects of the Mouse-Derived Exosomes of the Disclosure in Improving the Microenvironment in Tumors Firstly, 6-8 weeks old male C57BL/6 mice (purchased from Vital River Laboratory Animal Technology Co., Ltd.)

were selected, and $5\times10^5$ of E.G7 lymphoma cells (purchased from ATCC cell bank) were subcutaneously injected on day 0 into the left axillary sites of the mice to construct an E.G7 lymphoma model. On day 7, the mice with similar tumor volumes were selected and randomly grouped. The hybrid exosomes (nc-lps-exo) in Example 5 were intratumorally injected into mouse E.G7 tumors having the same volume, and the situations of the infiltration of various immune cells in the tumors were investigated; and meanwhile the following control groups were set up: a PBS group, a group of untreated macrophage-derived exosomes (pbs-exo), a group of the exosomes in Example 5 without lipopolysaccharide stimulation (nc-exo), and a group of macrophage-derived exosomes only stimulated with a lipopolysaccharide (lps-exo). The injection was carried out every other day, each injection dose was $3.7\times10^9$, and totally there were three injections. On day 14, the mice were sacrificed, the tumor tissues were taken out and ground, followed by lysing red blood cells and washing, and a single cell suspension was obtained.

Figure 17:
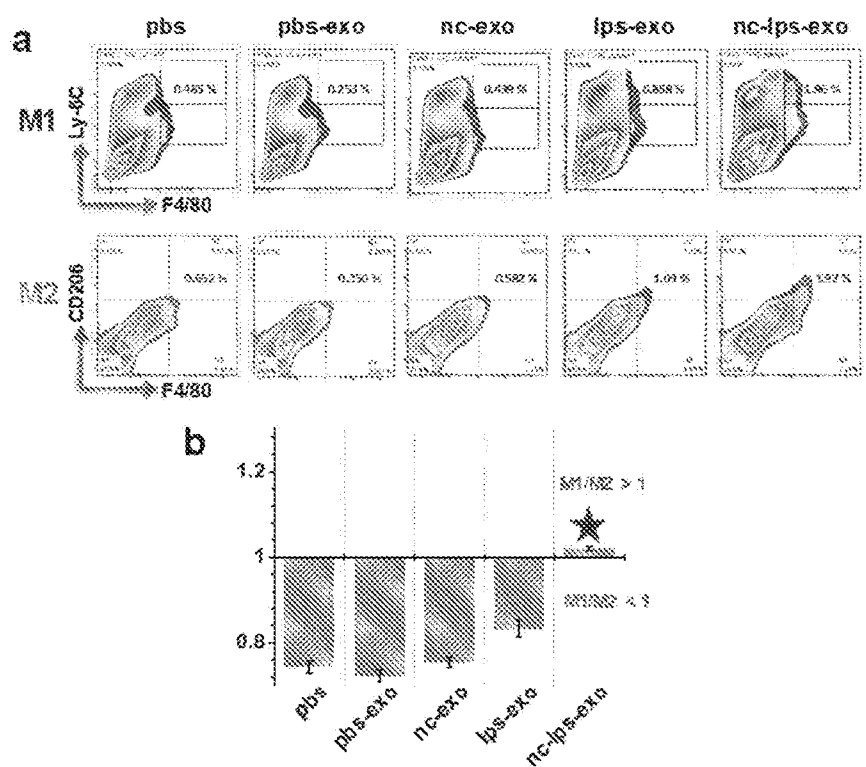
FIG. 17 shows the influence on the typing of tumor-associated macrophages (M1/M2) after the intratumorally injection of mouse-derived exosomes of the disclosure.

Then the single cell suspension was stained and the proportions of different immune cells were analyzed. The specific staining protocols were as follows: For the tumor-associated macrophages: the cells of the tumor cell suspension were incubated in the dark for 25 min (4°) using 0.25 μg of Pacific Blue-labeled anti-F4/80, 0.25 μg of APC-labeled anti-Ly-6C, and 0.25 μg of Alex Fluro 488-labeled anti-CD206 antibodies (all of the antibodies for flow cytometry were from ebioscience) and washed twice with a stain buffer (purchased from ebioscience), the cell suspension was detected using a flow cytometer to analyze the proportions of $F4/80^+Ly\text{-}6C^+$ double positive macrophages (M1) and $F4/80^+$ $CD206^+$ double positive macrophages (M2), in which 500,000 cells were collected for analysis for each sample, and the experimental results were shown in FIG. 17.

Figure 18:
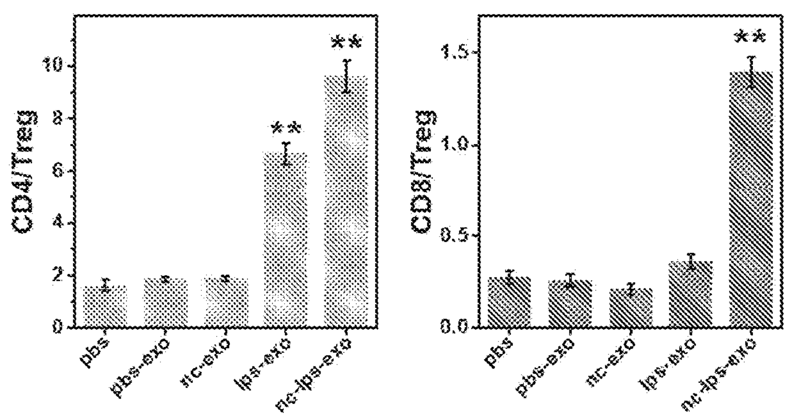
FIG. 18 shows ratios of CD4/Tregs and CD8/Tregs in the tumor after the intratumor injection of the mouse-derived exosomes of the disclosure.

For the regulatory T cells: firstly, the cells of the tumor cell suspension were incubated in the dark for 25 min (4° C.) using 0.25 μg of BV510-labeled anti-CD3, 0.25 μg of PerCP-Cy5.5-labeled anti-CD4, 0.25 μg of PE labeled anti-CD8, and 0.25 μg of FTIC-labeled anti-CD25 antibodies (all of the antibodies for flow cytometry were purchased from ebioscience) and washed once with a stain buffer (purchased from ebioscience), followed by adding a fixation buffer (purchased from ebioscience) and incubating in the dark for 20 min, adding a permeabilization buffer (purchased from ebioscience), subjecting to centrifugation, adding an Alex Fluro700-labeled anti-Foxp3 antibody (purchased from ebioscience) and incubating in the dark for 30 min, then adding the permeabilization buffer and washing, resuspending with the stain buffer (purchased from ebioscience), detecting the cell suspension using a flow cytometer, and analyzing the proportions of $CD4^+$ $CD25^+Foxp3^+$ (regulatory T cells), $CD3^+CD4^+$ and $CD3^+$ $CD8^+$ T cells, in which 500,000 cells were collected for analysis for each sample, and the experimental results were shown in FIG. 18.

Figure 19:
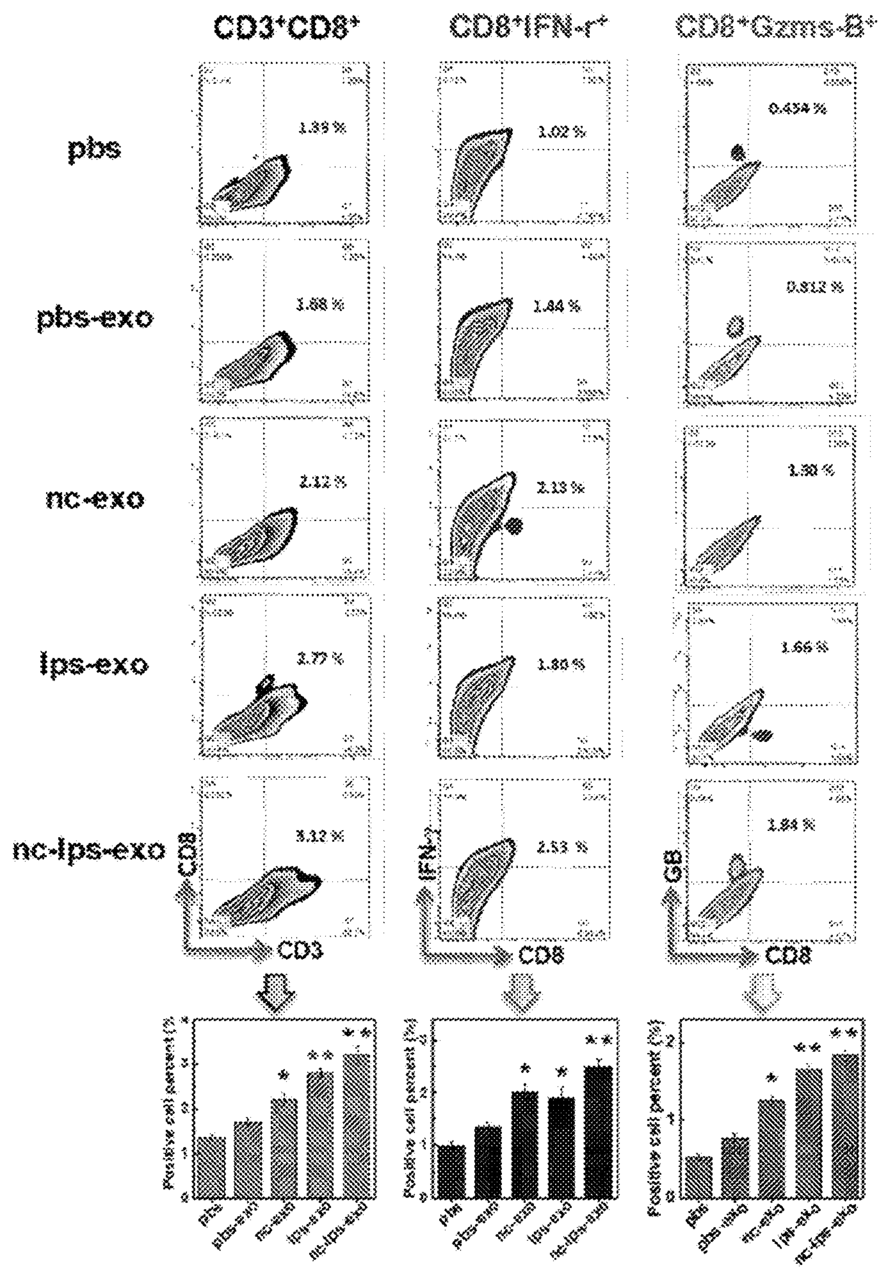
FIG. 19 shows situations of CTL infiltration in the tumor after the intratumor injection of the mouse-derived exosomes of the disclosure.

For the cytotoxic T cells: firstly, the cells of the tumor cell suspension were incubated in the dark for 25 min (4° C.) using 0.25 μg of BV510-labeled anti-CD3 and 0.25 μg of eF450-labeled anti-CD8 antibodies (all of the antibodies for flow cytometry were purchased from ebioscience) and washed once with a stain buffer (purchased from ebioscience), followed by adding a fixation buffer (purchased from ebioscience) and incubating in the dark for 20 min, adding a permeabilization buffer (purchased from ebioscience), subjecting to centrifugation, adding a PE-labeled anti-IFN-γ antibody and an APC-labeled anti-Gzms-B antibody (purchased from ebioscience) and incubating in the dark for 30 min, then adding the permeabilization buffer and washing, resuspending with the stain buffer (purchased from ebioscience), detecting the cell suspension using a flow cytometer, and analyzing the proportions of $CD3^+CD8^+$ double positive, $CD8^+$ $TFN\text{-}\gamma^+$ double positive and $CD8^+$ $Gzms\text{-}B^+$ double positive T cells, in which 500,000 cells were collected for analysis for each sample, and the experimental results were shown in FIG. 19.

It can be seen from FIG. 17*a* that, as compared with the pbs group, the proportions of both M1-type macrophages and M2-type macrophages in the tumors in the hybrid exosome group (nc-lps-exo) were increased, which was because both of the exosomes comprised a large number of chemokines, which can chemoattract more macrophages to infiltrate into the tumors. The macrophages chemoattracted to the tumor sites will be differentiated into different types under the induction of the surrounding environment, the ratios of M1-type macrophages to M2-type macrophages (M1/M2) in each group of TAMs can reflect that which type of the macrophages occupied a dominant position in the tumors, meaning that M2-type macrophages occupied a dominant position when the value of M1/M2 was less than 1, and M1-type macrophages occupied a dominant position when the value of M1/M2 was greater than 1. The calculation results of M1/M2 in the tumors of various groups were shown in FIG. 17*b*; it can be seen from the figure that, as compared with the M1/M2 ratio (0.74) of the pbs-exo group, the M1/M2 ratio of the nc-lps-exo group was greater than 1, indicating that the M1-type macrophages in the tumors of this group had occupied a dominant position after intratumoral injection of nc-lps-exo. In addition, FIG. 18 showed significantly increased ratios of CD4/Tregs and CD8/Tregs within the tumors of the mice after intratumoral injection of hybrid exosomes nc-lps-exo, indicating that the infiltration degree of Treg cells with the immunosuppressive ability inside the tumors were weakened after the administration of hybrid exosomes nc-lps-exo. Since M1-type macrophages in the tumors of the group of nc-lps-exo injection occupied a dominant position and the infiltration of Treg cells was reduced, the immunosuppressive microenvironment was improved to a certain extent, thus providing a suitable "soil" for the infiltration of effector T cells in the tumors. FIG. 19 showed greatly increased proportions of CD8 T, $CD8^+$ $IFN\text{-}r^+$ double positive and $CD8^+GB^+$ double positive CTLs in the tumors of the hybrid exosome nc-lps-exo group, demonstrating that a large number of CTLs in the tumors had infiltrated into the tumors, which laid a good foundation for subsequently effective tumor cells killing.

Example 18. Effects of Human-Derived Exosomes of the Disclosure in Improving the Microenvironment in 3D Tumor Cell Spheroids The tumor microenvironment in a human body was simulated in vitro by preparing 3D cell spheroids using human-derived tumor cells, M2 human macrophages and human T cells, meanwhile the exosomes of the disclosure were added for stimulation, the proportions of M1/M2-type macrophages and the proportions of Tregs in the 3D cell spheroids were detected, and the sizes of the 3D cell spheroids were investigated by microscopic imaging. The specific steps were as follows:

(a) Preparation and culture of three types of cells: 50 mL of peripheral blood was collected from a healthy human by means of venous blood collection using a sterile blood collection needle, the human monocytes were extracted and the human macrophages were induced using the method in item (b) of Example 4, and then the human-derived macrophages were stimulated by adding IL-4 (20 ng/mL) to induce the macrophages into M2-type macrophages; meanwhile, the human peripheral blood T cells were sorted and collected using the method in Example 4; and a DMEM complete medium in item (a) of Example 4 was used to culture A375 melanoma.

(b) Coating a 96-well plate using agarose gel: 10 mL of DMEM incomplete medium was taken and 0.15 g agarose was added, and heated to 100° C. for 1 h to melt the agarose. The prepared agarose was added to the 96-well plate after the solution has been cooled for a period of time but not completely solidified, and the agarose was allowed to be cooled to room temperature to form concave cell culture substrates.

(c) Culture of 3D cell spheroids and administration of human-derived exosomes: the human-derived tumor cells, M2 human macrophages and human T cells were mixed at a ratio of 700:300:300, then added to the above 96-well plates pre-plated with the substrate gel and cultured; the hybrid exosomes of the disclosure (h-nc-lps-exo) were added after the mixed 3D cell spheroids had an initial appearance, and meanwhile the following control groups were set up for stimulation: a PBS group, a group of untreated human-derived macrophage-derived exosomes (h-pbs-exo), a group of the exosomes in Example 9 without lipopolysaccharide stimulation (h-nc-exo), and a group of human-derived macrophage-derived exosomes only stimulated by a lipopolysaccharide (h-lps-exo).

(d) Detection of proportions of M1/M2 and proportions of Tregs: the 3D cell spheroids of different groups were taken to prepare single cell suspensions, the single cell suspensions were stained and the proportions of different immune cells were analyzed. The specific staining protocols were as follows: 1. The cell suspensions were incubated in the dark for 25 min (4° C.) using 0.25 μg of PE-Cy7-labeled anti-CD11b, 0.25 μg of eFlour450-labeled anti-CD14, 0.25 μg of APC-labeled anti-CD163 and 0.25 μg of PE-labeled anti-CD86 antibodies (all of the antibodies for flow cytometry were from ebioscience) and washed twice with a stain buffer (purchased from ebioscience), the cell suspensions were detected using a flow cytometer, and the proportions of $CD86^+$ $CD163^-$ (M1) and $CD86^-CD163^+$ (M2) macrophages in the $CD14^+$ $CD11b^+$ double positive macrophages were analyzed, in which 500,000 cells were collected for analysis for each sample, and the experimental results were shown in FIG. 20; 2. the cells of the tumor cell suspension were incubated in the dark for 25 min (4° C.) using 0.25 μg of BV605-labeled anti-CD3, 0.25 μg of PE-Cy7-labeled anti-CD4, 0.25 μg of APC-eFlour780 labeled anti-CD8 and 0.25 μg of APC-labeled anti-CD25 antibodies (all of the antibodies for flow cytometry were purchased from ebioscience) and washed once with a stain buffer (purchased from ebioscience), followed by adding a fixation buffer (purchased from ebioscience) and incubating in the dark for 20 min, adding a permeabilization buffer (purchased from ebioscience), subjecting to centrifugation, adding a PE-labeled anti-Foxp3 antibody (purchased from ebioscience) and incubating in the dark for 30 min, then adding the permeabilization buffer and washing, resuspending with the stain buffer (purchased from ebioscience), detecting the cell suspension using a flow cytometer, and analyzing the proportions of $CD4^+CD25^+$ $Foxp3^+$ (regulatory T cells), in which 100,000 cells were collected for analysis for each sample, and the experimental results were shown in FIG. 21.

Figure 22:
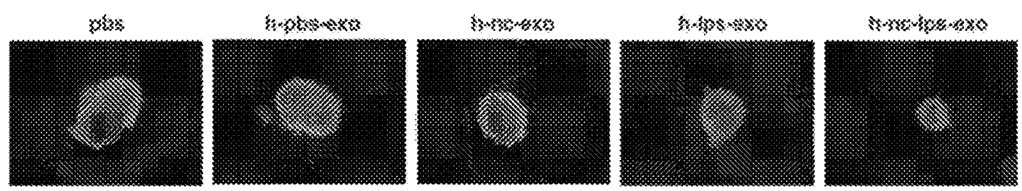
FIG. 22 shows volumes increase curves of 3D human tumor cell spheroids which have been stimulated with human-derived exosomes of the disclosure.

(e) Recording for volume changes and microscopic imaging of 3D cell spheroids: the 3D cell spheroids were gently aspirated and fixed overnight using 4% paraformaldehyde, then nuclear staining was carried out using Hoechst (purchased from Solarbio), followed by standing for 15 min at room temperature and transferring the cell spheroids to a well plate for fluorescence imaging, and the experimental results were shown in FIG. 22.

Figure 20:
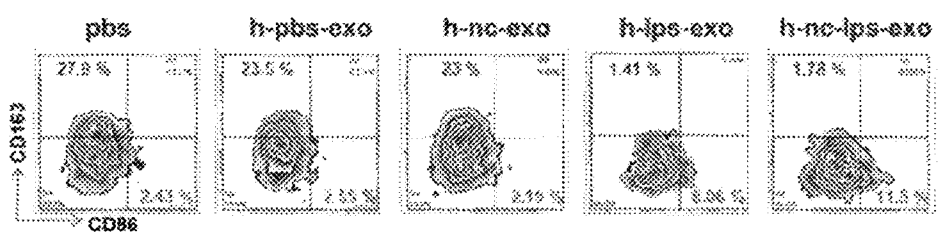
FIG. 20 shows the influence on the typing of the macrophages in 3D human tumor cell spheroids after the stimulation of the human-derived exosomes of the disclosure.
Figure 21:
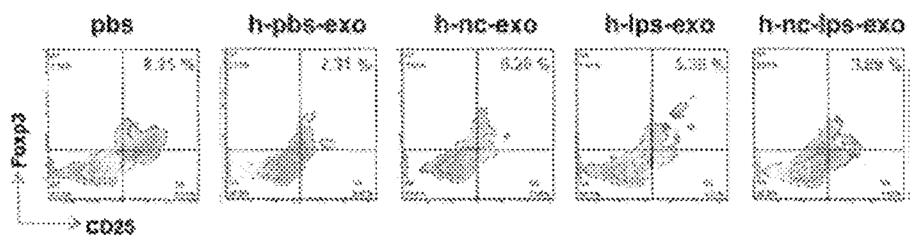
FIG. 21 shows proportions of Tregs in 3D human tumor cell spheroids which have been stimulated with human-derived exosomes of the disclosure.

It can be seen from FIG. 20 that, as compared with the pbs group, the proportion of M2-type macrophages in the 3D tumor cell spheroids of the group of the human-derived hybrid exosomes (h-nc-lps-exo) decreased significantly, and the proportion of M1-type macrophages increased, indicating that h-nc-lps-exo can induce the macrophages in the 3D cell spheroids towards M1-type macrophages. In addition, FIG. 21 showed that the proportions of $CD25^+$ $Foxp3^+$ Tregs in the 3D tumor cell spheroids of the group of human-derived hybrid exosomes (h-nc-lps-exo) decreased to 3.89% from 8.25% in the pbs group, indicating that the infiltration degrees of the Treg cells having the immunosuppressive ability in the 3D cell spheroids were reduced after the administration of human-derived hybrid exosomes h-nc-lps-exo. This is due to the presence of the cytokines for immune activation in h-nc-lps-exo, so that the immunosuppressive microenvironment was improved to a certain extent, thus providing a suitable "soil" for the effector T cells to exert killing effects in the tumors. It can be seen from the images of the final 3D cell spheroids in FIG. 22 that the diameter of the 3D cell spheroids of the h-nc-lps-exo group was the smallest and the tumor growth inhibitory effect was the most obvious.

Example 19. Animal Experiment Effects of Mouse-Derived Exosomes of the Disclosure 6-8 weeks old male C57BL/6 mice (purchased from Vital River Laboratory Animal Technology Co., Ltd.) were taken and inoculated with lymphoma cell E.G7-OVA tumor cells ($5\times10^5$) on day 0, immunized subcutaneously on day 5 using the hybrid exosome vaccine formulation prepared in Example 5, with a single inoculation amount of $3.7\times10^9$ exosomes in a single time; and additionally, a booster immunization group that received a second booster immunization (2 nc-lps-exo) was set up, in which a booster vaccination was carried out on day 8. At the same time, the following control groups were set up: a PBS group, a group of untreated macrophage-derived exosomes (pbs-exo), a group of the exosomes of the hybrid cells prepared in Example 5 without lipopolysaccharide stimulation (nc-exo), and a group of macrophage-derived exosomes only stimulated by a lipopolysaccharide (lps-exo), in which the injection doses of the exosomes in the control groups were $3.7\times10^9$ as well. Afterwards, the tumor volumes and the survival situations of the mice were recorded, and the results were shown in FIG. 23 and FIG. 24.

Figure 23:
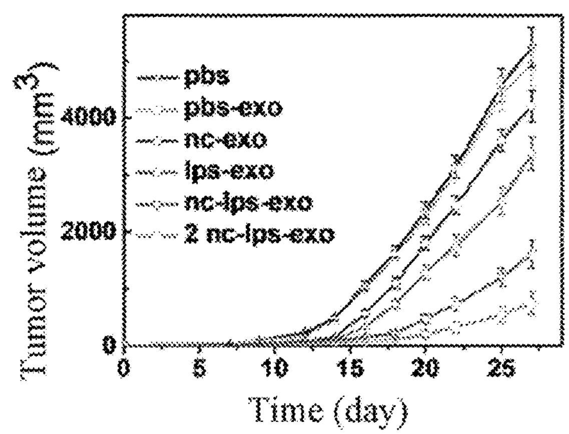
FIG. 23 shows tumor growth curves for E.G7-OVA tumor-bearing mice after the subcutaneous injection of the mouse-derived exosomes of the disclosure.
Figure 24:
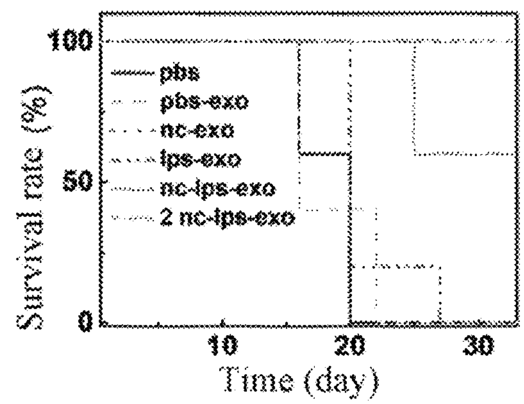
FIG. 24 shows survival time curves for E.G7-OVA tumor-bearing mice after the subcutaneous injection of the mouse-derived exosomes of the disclosure.

It can be seen from FIG. 23 and FIG. 24 that the inoculation of the hybrid exosomes of the disclosure can significantly reduce the tumor volumes of the mice; and the vaccine formulation can more effectively delay the tumor growth and prolong the average survival time of the mice after the booster treatment by the second immunization.

Example 20. Animal Experiment Effects of the Combination of Mouse-Derived Exosomes of the Disclosure and an Anti-PD-1 Antibody The combination therapy of the exosomes of the hybrid cells prepared in Example 7 of the disclosure and a PD-1 antibody was investigated for the immunotherapy trials of malignant melanoma, and the method was as follows:

6-8 weeks old male C57BL/6 mice (purchased from Vital River Laboratory Animal Technology Co., Ltd.) were taken and inoculated with Muc1-B16 melanoma cells (purchased from ATCC) on day 0 at an inoculation dose of $5\times10^5$ to construct an in-situ growth model of Muc1-B16 melanoma. The hybrid exosomes prepared in Example 7 were used in combination with an PD-1 antibody (a-PD1+vac.) for treatment, wherein exosomes were administered subcutaneously at a dose of $1.85\times10^9$ exosomes, the time for the first immunization was on day 5 after inoculating the tumor cells, and the time for the second immunization was on day 8; and the PD-1 antibody (purchased from BioXell) was administered intraperitoneally at a single administration dose of 100 μg on day 3, day 6, day 9, and day 12 respectively after inoculating the tumor cells. At the same time, the following three control groups were set up: a blank group (pbs), a single treatment group of the hybrid exosomes at double doses (2× vac.) and a single treatment group of the PD-1 antibody at double doses (2× a-PD1). Afterwards, the tumor volumes of the mice were recorded and the results were shown in FIG. 25.

6-8 weeks old male C57BL/6 mice (purchased from Vital River Laboratory Animal Technology Co., Ltd.) were taken and inoculated with Muc1-B16 melanoma cells (purchased from ATCC) on day 0 via tail veins at an inoculation dose of $1\times10^5$ to construct a lung metastasis model of Muc1-B16 melanoma. The hybrid exosomes prepared in Example 7 were used in combination with a PD-1 antibody (a-PD1+vac.) for treatment, wherein exosomes were administered subcutaneously at a dose of $1.85\times10^9$ exosomes, the time for the first immunization was on day 0, i.e., the day injecting the tumor cells via tail veins, and the time for the second immunization was on day 3; and the anti-PD-1 antibody (purchased from BioXell) of the single administration group was administered intraperitoneally at a single administration dose of 100 μg on day 0, day 3, day 6, and day 9 respectively after inoculating the tumor cells. At the same time, the following three control groups were set up: a blank group (pbs), a single treatment group of the hybrid exosomes at double doses (2× vac.) and a single treatment group of the PD-1 antibody at double doses (2× a-PD1). Afterwards, the body weight of the mice and the metastatic spots in lungs were recorded and the results were shown in FIG. 26 and FIG. 27.

Figure 25:
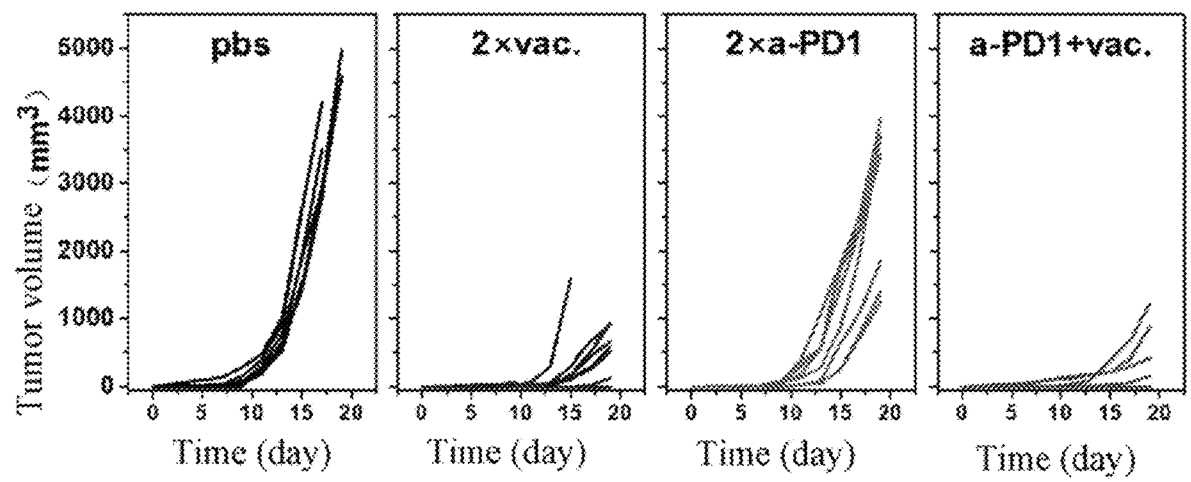
FIG. 25 shows tumor growth curves for Muc1-B16 tumor-bearing mice after the subcutaneous injection of the mouse-derived exosomes of the disclosure.

It can be seen from FIG. 25 that, when the anti-PD-1 antibody and the hybrid exosomes were used in combination for treatment, the growth of B16 melanoma in the mice of this group was inhibited to the greatest extent, only 4 mice in 8 mice appeared relatively small tumors at the end of observation, and the therapeutic effect was significantly superior to the therapeutic effects of the group of the PD-1 antibody at double doses and the single administration group of the exosomes at double doses.

Figure 26:
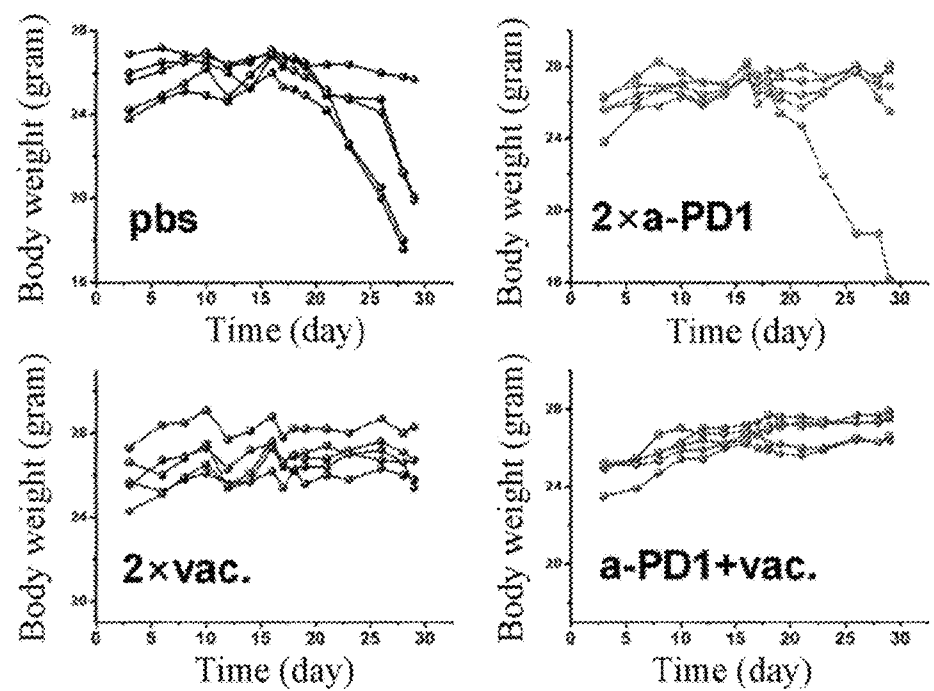
FIG. 26 shows body weight changes of Muc1-B16 tumor metastasis model mice after the subcutaneous injection of the mouse-derived exosomes of the disclosure.
Figure 27:
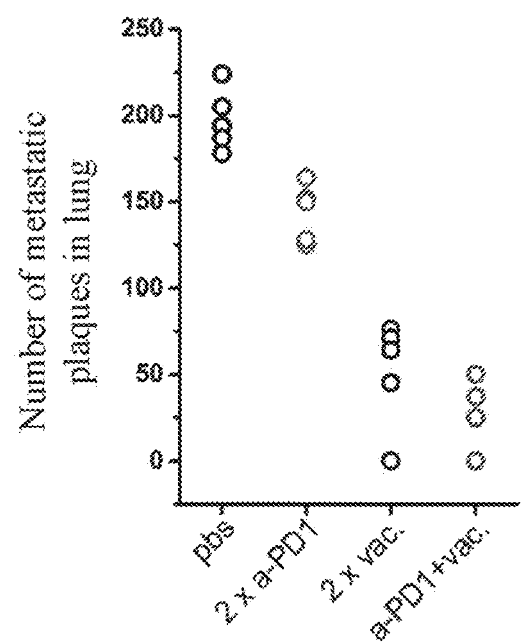
FIG. 27 shows statistics of the number of metastatic plaques in the lungs of the Muc1-B16 tumor metastasis model mice after the subcutaneous injection of the mouse-derived exosomes of the disclosure.

It can be seen from FIG. 26 and FIG. 27 that the body weight of the mice in the group of combination treatment of the PD-1 antibody and the hybrid exosomes increased steadily during the observation period, and the results for the counts of metastatic nodules in the mice lungs showed that the number of the metastatic nodules of melanoma in the mice lungs of this group was significantly reduced, and was significantly lower than those of the single administration group of the PD-1 antibody at double doses and the single administration group of the hybrid exosomes at double doses, indicating that the therapeutic effect in the group of combination treatment was the best. The above results indicated that there were synergistic inhibitory effects on both in-situ tumor growth and lung metastasis of the tumor when the hybrid exosome formulation was used in combination with the PD-1 antibody, with a therapeutic effect significantly superior to that of the single administration group of PD-1 or the exosomes at double doses.

From the analysis, it was believed that the reason for the synergistic effects lied in that the M2-type macrophages inside the tumors in the single hybrid exosome immunization group can not be eliminated by one hundred percent, although the hybrid exosomes reduce the proportions of M2-type macrophages; the remaining M2-type macrophages and the tumor cells, by means of the PD-L1 molecules on the surfaces, can bind the PD-1 molecules on the surface of the CTLs infiltrating into the tumors, so as to make the CTLs exhausted and lose the ability of killing tumors. However, the combined use of the PD-1 antibody can block the binding of PD-L1 and PD-1, and play synergistic effect with the hybrid exosomes, thereby reducing the exhaustion of the CTLs, allowing the CTLs to exert their natural tumor killing effects and enhancing the tumor inhibitory effects.

What is claimed is:

1. A method of preparing an exosome, the method comprising:

a) extracting nuclei from isolated tumor cells;

b) adding the nuclei to antigen presenting cells (APCs) in culture such that hybrid cells are obtained;

c) incubating the hybrid cells obtained in step b);

d) collecting supernatant from the culture medium comprising the hybrid cells incubated in step c);

e) isolating exosomes from the supernatant.

2. The method of claim 1, wherein the APC is a dendritic cell, macrophage or B cell.

3. The method of claim 1, wherein lipopolysaccharide, monophosporyl lipid A or unmethylated CpG oligodeoxynucleotide is added to the culture of step b).

* * * * *